US007777612B2

(12) United States Patent
Sampson et al.

(10) Patent No.: US 7,777,612 B2
(45) Date of Patent: Aug. 17, 2010

(54) THEFT PREVENTION DEVICE FOR AUTOMOTIVE VEHICLE SERVICE CENTERS

(75) Inventors: William G. Sampson, Elmhurst, IL (US); John S. Philbrook, Cornelius, NC (US)

(73) Assignee: Midtronics, Inc., Willowbrook, IL (US)

( * ) Notice: Subject to any disclaimer, the term of this patent is extended or adjusted under 35 U.S.C. 154(b) by 317 days.

(21) Appl. No.: 11/498,703

(22) Filed: Aug. 3, 2006

(65) Prior Publication Data

US 2006/0267575 A1 Nov. 30, 2006

Related U.S. Application Data

(63) Continuation-in-part of application No. 10/823,140, filed on Apr. 13, 2004, now Pat. No. 7,119,686.

(60) Provisional application No. 60/705,389, filed on Aug. 4, 2005.

(51) Int. Cl.

| | |
|---|---|
| ***B60R 25/10*** | (2006.01) |
| ***G08B 13/14*** | (2006.01) |
| ***G08B 23/00*** | (2006.01) |
| ***A61B 5/00*** | (2006.01) |
| ***H04M 1/66*** | (2006.01) |
| ***E21B 15/04*** | (2006.01) |

(52) U.S. Cl. .............. 340/426.1; 340/572.1; 340/573.1; 600/300; 379/199; 173/2

(58) Field of Classification Search .............. 340/426.1, 340/572.1, 573.1; 600/300; 379/199; 173/2
See application file for complete search history.

(56) References Cited

U.S. PATENT DOCUMENTS

| | | | | |
|---|---|---|---|---|
| 2,000,665 | A | 5/1935 | Neal | 439/440 |
| 2,417,940 | A | 3/1947 | Lehman | 200/61.25 |
| 2,514,745 | A | 7/1950 | Dalzell | 324/115 |
| 2,727,221 | A | 12/1955 | Springg | 340/447 |
| 3,178,686 | A | 4/1965 | Mills | 340/447 |
| 3,223,969 | A | 12/1965 | Alexander | 340/447 |
| 3,267,452 | A | 8/1966 | Wolf | 340/249 |
| 3,356,936 | A | 12/1967 | Smith | 324/429 |

(Continued)

FOREIGN PATENT DOCUMENTS

DE 196 38 324 9/1996

(Continued)

OTHER PUBLICATIONS

"Electrochemical Impedance Spectroscopy in Battery Development and Testing", *Batteries International*, Apr. 1997, pp. 59 and 62-63.

(Continued)

*Primary Examiner*—Daniel Wu
*Assistant Examiner*—John F Mortell
(74) *Attorney, Agent, or Firm*—Westman, Champlin & Kelly, P.A.

(57) ABSTRACT

An apparatus and method for preventing theft in automotive vehicle service centers. The apparatus includes at least one portable tool and a controller. The portable tool includes circuitry configured to communicate with the controller. The portable tool further includes anti-theft circuitry, which is configured to disable the portable tool if no communication occurs between the portable tool and the controller for a predetermined time period.

8 Claims, 8 Drawing Sheets

U.S. PATENT DOCUMENTS

| | | | | |
|---|---|---|---|---|
| 3,562,634 | A | 2/1971 | Latner | 324/427 |
| 3,593,099 | A | 7/1971 | Scholl | 320/127 |
| 3,607,673 | A | 9/1971 | Seyl | 324/425 |
| 3,652,341 | A | 3/1972 | Halsall et al. | 29/623.2 |
| 3,676,770 | A | 7/1972 | Sharaf et al. | 324/430 |
| 3,729,989 | A | 5/1973 | Little | 73/862.192 |
| 3,750,011 | A | 7/1973 | Kreps | 324/430 |
| 3,753,094 | A | 8/1973 | Furuishi et al. | 324/430 |
| 3,776,177 | A | 12/1973 | Bryant et al. | 116/311 |
| 3,796,124 | A | 3/1974 | Crosa | 411/521 |
| 3,808,522 | A | 4/1974 | Sharaf | 324/430 |
| 3,811,089 | A | 5/1974 | Strezelewicz | 324/170 |
| 3,816,805 | A | 6/1974 | Terry | 320/123 |
| 3,850,490 | A | 11/1974 | Zehr | 439/822 |
| 3,873,911 | A | 3/1975 | Champlin | 324/430 |
| 3,876,931 | A | 4/1975 | Godshalk | 324/429 |
| 3,886,426 | A | 5/1975 | Daggett | 320/117 |
| 3,886,443 | A | 5/1975 | Miyakawa et al. | 324/426 |
| 3,889,248 | A | 6/1975 | Ritter | 340/636.11 |
| 3,906,329 | A | 9/1975 | Bader | 320/134 |
| 3,909,708 | A | 9/1975 | Champlin | 324/431 |
| 3,936,744 | A | 2/1976 | Perlmutter | 324/772 |
| 3,946,299 | A | 3/1976 | Christianson et al. | 320/430 |
| 3,947,757 | A | 3/1976 | Grube et al. | 324/416 |
| 3,969,667 | A | 7/1976 | McWilliams | 324/427 |
| 3,979,664 | A | 9/1976 | Harris | 324/397 |
| 3,984,762 | A | 10/1976 | Dowgiallo, Jr. | 324/430 |
| 3,984,768 | A | 10/1976 | Staples | 324/712 |
| 3,989,544 | A | 11/1976 | Santo | 429/65 |
| 4,008,619 | A | 2/1977 | Alcaide et al. | 73/724 |
| 4,023,882 | A | 5/1977 | Pettersson | 439/426 |
| 4,024,953 | A | 5/1977 | Nailor, III | 206/344 |
| 4,047,091 | A | 9/1977 | Hutchines et al. | 363/59 |
| 4,053,824 | A | 10/1977 | Dupuis et al. | 324/434 |
| 4,056,764 | A | 11/1977 | Endo et al. | 320/101 |
| 4,057,313 | A | 11/1977 | Polizzano | 439/219 |
| 4,070,624 | A | 1/1978 | Taylor | 324/772 |
| 4,086,531 | A | 4/1978 | Bernier | 324/772 |
| 4,106,025 | A | 8/1978 | Katz | 343/715 |
| 4,112,351 | A | 9/1978 | Back et al. | 324/380 |
| 4,114,083 | A | 9/1978 | Benham et al. | 340/636.13 |
| 4,126,874 | A | 11/1978 | Suzuki et al. | 396/301 |
| 4,160,916 | A | 7/1979 | Papasideris | 307/10.6 |
| 4,178,546 | A | 12/1979 | Hulls et al. | 324/772 |
| 4,193,025 | A | 3/1980 | Frailing et al. | 324/427 |
| 4,207,611 | A | 6/1980 | Gordon | 701/33 |
| 4,217,645 | A | 8/1980 | Barry et al. | 702/63 |
| 4,280,457 | A | 7/1981 | Bloxham | 123/198 R |
| 4,297,639 | A | 10/1981 | Branham | 324/429 |
| 4,307,342 | A | 12/1981 | Peterson | 324/767 |
| 4,315,204 | A | 2/1982 | Sievers et al. | 322/28 |
| 4,316,185 | A | 2/1982 | Watrous et al. | 340/636.11 |
| 4,322,685 | A | 3/1982 | Frailing et al. | 324/429 |
| 4,351,405 | A | 9/1982 | Fields et al. | 180/65.2 |
| 4,352,067 | A | 9/1982 | Ottone | 324/434 |
| 4,360,780 | A | 11/1982 | Skutch, Jr. | 324/437 |
| 4,361,809 | A | 11/1982 | Bil et al. | 324/426 |
| 4,363,407 | A | 12/1982 | Buckler et al. | 209/3.3 |
| 4,369,407 | A | 1/1983 | Korbell | 324/416 |
| 4,379,989 | A | 4/1983 | Kurz et al. | 320/165 |
| 4,379,990 | A | 4/1983 | Sievers et al. | 322/99 |
| 4,385,269 | A | 5/1983 | Aspinwall et al. | 320/129 |
| 4,390,828 | A | 6/1983 | Converse et al. | 320/153 |
| 4,392,101 | A | 7/1983 | Saar et al. | 320/156 |
| 4,396,880 | A | 8/1983 | Windebank | 320/156 |
| 4,408,157 | A | 10/1983 | Beaubien | 324/712 |
| 4,412,169 | A | 10/1983 | Dell'Orto | 320/123 |
| 4,423,378 | A | 12/1983 | Marino et al. | 324/427 |
| 4,423,379 | A | 12/1983 | Jacobs et al. | 324/429 |
| 4,424,491 | A | 1/1984 | Bobbett et al. | 324/433 |
| 4,441,359 | A | 4/1984 | Ezoe | 73/116.06 |
| 4,459,548 | A | 7/1984 | Lentz et al. | 324/472 |
| 4,514,694 | A | 4/1985 | Finger | 324/429 |
| 4,520,353 | A | 5/1985 | McAuliffe | 340/636.16 |
| 4,521,498 | A | 6/1985 | Juergens | 429/59 |
| 4,564,798 | A | 1/1986 | Young | 320/103 |
| 4,620,767 | A | 11/1986 | Woolf | 439/217 |
| 4,633,418 | A | 12/1986 | Bishop | 702/63 |
| 4,637,359 | A | 1/1987 | Cook | 123/179 |
| 4,659,977 | A | 4/1987 | Kissel et al. | 320/150 |
| 4,663,580 | A | 5/1987 | Wortman | 320/153 |
| 4,665,370 | A | 5/1987 | Holland | 324/429 |
| 4,667,143 | A | 5/1987 | Cooper et al. | 320/153 |
| 4,667,279 | A | 5/1987 | Maier | 363/46 |
| 4,678,998 | A | 7/1987 | Muramatsu | 324/427 |
| 4,679,000 | A | 7/1987 | Clark | 324/428 |
| 4,680,528 | A | 7/1987 | Mikami et al. | 320/165 |
| 4,686,442 | A | 8/1987 | Radomski | 320/123 |
| 4,697,134 | A | 9/1987 | Burkum et al. | 320/134 |
| 4,707,795 | A | 11/1987 | Alber et al. | 702/63 |
| 4,709,202 | A | 11/1987 | Koenck et al. | 320/112 |
| 4,710,861 | A | 12/1987 | Kanner | 363/46 |
| 4,719,428 | A | 1/1988 | Liebermann | 324/436 |
| 4,723,656 | A | 2/1988 | Kiernan et al. | 206/705 |
| 4,743,855 | A | 5/1988 | Randin et al. | 324/430 |
| 4,745,349 | A | 5/1988 | Palanisamy et al. | 320/125 |
| 4,773,011 | A | 9/1988 | VanHoose | 701/30 |
| 4,781,629 | A | 11/1988 | Mize | 439/822 |
| 4,816,768 | A | 3/1989 | Champlin | 324/428 |
| 4,820,966 | A | 4/1989 | Fridman | 320/116 |
| 4,825,170 | A | 4/1989 | Champlin | 324/436 |
| 4,847,547 | A | 7/1989 | Eng, Jr. et al. | 320/153 |
| 4,849,700 | A | 7/1989 | Morioka et al. | 324/427 |
| 4,874,679 | A | 10/1989 | Miyagawa | 429/91 |
| 4,876,495 | A | 10/1989 | Palanisamy et al. | 320/106 |
| 4,881,038 | A | 11/1989 | Champlin | 324/426 |
| 4,885,523 | A | 12/1989 | Koench | 230/131 |
| 4,888,716 | A | 12/1989 | Ueno | 702/63 |
| 4,901,007 | A | 2/1990 | Sworm | 324/110 |
| 4,907,176 | A | 3/1990 | Bahnick et al. | 364/551.01 |
| 4,912,416 | A | 3/1990 | Champlin | 324/430 |
| 4,913,116 | A | 4/1990 | Katogi et al. | 123/406.32 |
| 4,926,330 | A | 5/1990 | Abe et al. | 701/33 |
| 4,929,931 | A | 5/1990 | McCuen | 340/636.15 |
| 4,931,738 | A | 6/1990 | MacIntyre et al. | 324/435 |
| 4,932,905 | A | 6/1990 | Richards | 439/822 |
| 4,933,845 | A | 6/1990 | Hayes | 710/104 |
| 4,934,957 | A | 6/1990 | Bellusci | 439/504 |
| 4,937,528 | A | 6/1990 | Palanisamy | 324/430 |
| 4,947,124 | A | 8/1990 | Hauser | 324/430 |
| 4,949,046 | A | 8/1990 | Seyfang | 324/427 |
| 4,956,597 | A | 9/1990 | Heavey et al. | 320/129 |
| 4,965,738 | A | 10/1990 | Bauer et al. | 320/136 |
| 4,968,941 | A | 11/1990 | Rogers | 324/428 |
| 4,968,942 | A | 11/1990 | Palanisamy | 324/430 |
| 4,969,834 | A | 11/1990 | Johnson | 439/141 |
| 4,983,086 | A | 1/1991 | Hatrock | 411/259 |
| 5,004,979 | A | 4/1991 | Marino et al. | 324/160 |
| 5,030,916 | A | 7/1991 | Bokitch | 324/503 |
| 5,032,825 | A | 7/1991 | Kuznicki | 340/636.15 |
| 5,034,893 | A | 7/1991 | Fisher | 701/99 |
| 5,037,778 | A | 8/1991 | Stark et al. | 228/121 |
| 5,047,722 | A | 9/1991 | Wurst et al. | 324/430 |
| 5,081,565 | A | 1/1992 | Nabha et al. | 362/465 |
| 5,087,881 | A | 2/1992 | Peacock | 324/378 |
| 5,095,223 | A | 3/1992 | Thomas | 307/110 |
| 5,108,320 | A | 4/1992 | Kimber | 439/883 |
| 5,109,213 | A | 4/1992 | Williams | 340/447 |
| 5,126,675 | A | 6/1992 | Yang | 324/435 |
| 5,130,658 | A | 7/1992 | Bohmer | 324/435 |
| 5,140,269 | A | 8/1992 | Champlin | 324/433 |
| 5,144,218 | A | 9/1992 | Bosscha | 320/139 |
| 5,144,248 | A | 9/1992 | Alexandres et al. | 324/428 |
| 5,159,272 | A | 10/1992 | Rao et al. | 324/429 |

5,160,881 A 11/1992 Schramm et al. ............... 322/7
5,168,208 A 12/1992 Schultz et al. ................ 322/25
5,170,124 A 12/1992 Blair et al. .................. 324/434
5,179,335 A 1/1993 Nor .......................... 320/159
5,194,799 A 3/1993 Tomantschger ............. 320/103
5,204,611 A 4/1993 Nor et al. .................... 320/145
5,214,370 A 5/1993 Harm et al. ................. 320/152
5,214,385 A 5/1993 Gabriel et al. .............. 324/434
5,241,275 A 8/1993 Fang .......................... 324/430
5,254,952 A 10/1993 Salley et al. ................ 324/429
5,266,880 A 11/1993 Newland .................... 320/125
5,281,919 A 1/1994 Palanisamy ................ 324/427
5,281,920 A 1/1994 Wurst ......................... 324/430
5,295,078 A 3/1994 Stich et al. .................. 700/297
5,298,797 A 3/1994 Redl .......................... 327/387
5,300,874 A 4/1994 Shimamoto et al. ......... 320/106
5,302,902 A 4/1994 Groehl ....................... 324/434
5,313,152 A 5/1994 Wozniak et al. ............. 320/118
5,315,287 A 5/1994 Sol ........................... 340/455
5,321,626 A 6/1994 Palladino ..................... 702/63
5,321,627 A 6/1994 Reher .......................... 702/63
5,323,337 A 6/1994 Wilson et al. ................. 702/73
5,325,041 A 6/1994 Briggs ........................ 320/149
5,331,268 A 7/1994 Patino et al. ................ 320/158
5,332,927 A 7/1994 Paul et al. ..................... 307/66
5,336,993 A 8/1994 Thomas et al. ........... 324/158.1
5,338,515 A 8/1994 Dalla Betta et al. ........... 422/95
5,339,018 A 8/1994 Brokaw ...................... 320/147
5,343,380 A 8/1994 Champlin .................... 363/46
5,347,163 A 9/1994 Yoshimura ................... 307/66
5,352,968 A 10/1994 Reni et al. .................. 320/136
5,357,519 A 10/1994 Martin et al. .............. 371/15.1
5,365,160 A 11/1994 Leppo et al. ................ 320/160
5,365,453 A 11/1994 Startup et al. ................. 702/36
5,369,364 A 11/1994 Renirie et al. ............... 324/430
5,381,096 A 1/1995 Hirzel ........................ 324/427
5,387,871 A 2/1995 Tsai ........................... 324/429
5,402,007 A 3/1995 Center et al. .............. 290/40 B
5,410,754 A 4/1995 Klotzbach et al. ........... 370/466
5,412,308 A 5/1995 Brown ........................ 323/267
5,412,323 A 5/1995 Kato et al. .................. 324/429
5,425,041 A 6/1995 Seko et al. ............... 372/45.01
5,426,371 A 6/1995 Salley et al. ................ 324/429
5,426,416 A 6/1995 Jefferies et al. ............. 340/664
5,430,645 A 7/1995 Keller ................... 364/424.01
5,432,025 A 7/1995 Cox ............................ 429/65
5,432,426 A 7/1995 Yoshida ...................... 320/160
5,434,495 A 7/1995 Toko .......................... 320/135
5,435,185 A 7/1995 Eagan ......................... 73/587
5,442,274 A 8/1995 Tamai ........................ 320/146
5,445,026 A 8/1995 Eagan ......................... 73/591
5,449,996 A 9/1995 Matsumoto et al. ......... 320/148
5,449,997 A 9/1995 Gilmore et al. ............. 320/148
5,451,881 A 9/1995 Finger ........................ 324/433
5,453,027 A 9/1995 Buell et al. ................. 439/433
5,457,377 A 10/1995 Jonsson ...................... 324/430
5,459,660 A 10/1995 Berra .......................... 701/33
5,469,043 A 11/1995 Cherng et al. ............... 320/161
5,485,090 A 1/1996 Stephens .................... 324/433
5,488,300 A 1/1996 Jamieson .................... 324/432
5,504,674 A 4/1996 Chen et al. ..................... 705/4
5,508,599 A 4/1996 Koenck ...................... 320/138
5,519,383 A 5/1996 De La Rosa ........... 340/636.15
5,528,148 A 6/1996 Rogers ....................... 320/137
5,537,967 A 7/1996 Tashiro et al. ............ 123/192.1
5,541,489 A 7/1996 Dunstan ..................... 320/134
5,546,317 A 8/1996 Andrieu ....................... 702/63
5,548,273 A 8/1996 Nicol et al. ................. 340/439
5,550,485 A 8/1996 Falk .......................... 324/772
5,561,380 A 10/1996 Sway-Tin et al. ........... 324/509
5,562,501 A 10/1996 Kinoshita et al. ........... 439/852
5,563,496 A 10/1996 McClure ..................... 320/128
5,572,136 A 11/1996 Champlin ................... 324/426
5,573,611 A 11/1996 Koch et al. ............... 152/152.1
5,574,355 A 11/1996 McShane et al. ............ 320/161
5,578,915 A 11/1996 Crouch, Jr. et al. .......... 324/428
5,583,416 A 12/1996 Klang ........................ 320/160
5,585,416 A 12/1996 Audett et al. ................. 522/35
5,585,728 A 12/1996 Champlin ................... 324/427
5,589,757 A 12/1996 Klang ........................ 320/160
5,592,093 A 1/1997 Klingbiel .................... 324/426
5,592,094 A 1/1997 Ichikawa .................... 324/427
5,596,260 A 1/1997 Moravec et al. ............. 320/135
5,598,098 A 1/1997 Champlin ................... 324/430
5,602,462 A 2/1997 Stich et al. ................. 323/258
5,606,242 A 2/1997 Hull et al. ................... 320/106
5,614,788 A 3/1997 Mullins et al. ................ 315/82
5,621,298 A 4/1997 Harvey ....................... 320/134
5,633,985 A 5/1997 Severson et al. ............ 704/267
5,637,978 A 6/1997 Kellett et al. ................ 320/104
5,642,031 A 6/1997 Brotto ........................ 320/156
5,650,937 A 7/1997 Bounaga ...................... 702/65
5,652,501 A 7/1997 McClure et al. ........ 340/636.15
5,653,659 A 8/1997 Kunibe et al. ............... 477/111
5,654,623 A 8/1997 Shiga et al. ................. 320/106
5,656,920 A 8/1997 Cherng et al. ............... 324/431
5,661,368 A 8/1997 Deol et al. .................... 315/82
5,675,234 A 10/1997 Greene ................. 340/636.11
5,677,077 A 10/1997 Faulk .......................... 429/90
5,684,678 A 11/1997 Barrett ........................ 363/17
5,699,050 A 12/1997 Kanazawa ............. 340/636.13
5,701,089 A 12/1997 Perkins ....................... 324/772
5,705,929 A 1/1998 Caravello et al. ........... 324/430
5,707,015 A 1/1998 Guthrie ...................... 241/120
5,710,503 A 1/1998 Sideris et al. ............... 320/116
5,711,648 A 1/1998 Hammerslag ............... 414/800
5,717,336 A 2/1998 Basell et al. ................ 324/430
5,717,937 A 2/1998 Fritz .......................... 713/300
5,732,074 A 3/1998 Spaur et al. ................. 370/313
5,739,667 A 4/1998 Matsuda et al. ............. 320/128
5,744,962 A 4/1998 Alber et al. ................. 324/426
5,745,044 A 4/1998 Hyatt, Jr. et al. ........... 340/5.23
5,747,189 A 5/1998 Perkins ........................ 429/91
5,747,909 A 5/1998 Syverson et al. ....... 310/156.56
5,747,967 A 5/1998 Muljadi et al. .............. 320/148
5,754,417 A 5/1998 Nicollini ...................... 363/60
5,757,192 A 5/1998 McShane et al. ............ 324/427
5,760,587 A 6/1998 Harvey ....................... 324/434
5,772,468 A 6/1998 Kowalski et al. ............ 439/506
5,773,978 A 6/1998 Becker ....................... 324/430
5,778,326 A 7/1998 Moroto et al. ................ 701/22
5,780,974 A 7/1998 Pabla et al. ................... 315/82
5,780,980 A 7/1998 Naito ......................... 318/139
5,789,899 A 8/1998 van Phuoc et al. .......... 320/112
5,793,359 A 8/1998 Ushikubo ................... 345/169
5,796,239 A 8/1998 van Phuoc et al. .......... 320/107
5,808,469 A 9/1998 Kopera ....................... 324/434
5,811,979 A 9/1998 Rhein ......................... 324/718
5,818,234 A 10/1998 McKinnon .................. 324/433
5,820,407 A 10/1998 Morse et al. ................ 439/504
5,821,756 A 10/1998 McShane et al. ............ 324/430
5,821,757 A 10/1998 Alvarez et al. .............. 324/434
5,825,174 A 10/1998 Parker ........................ 324/106
5,831,435 A 11/1998 Troy .......................... 324/426
5,832,396 A 11/1998 Moroto et al. ................ 701/22
5,850,113 A 12/1998 Weimer et al. .............. 307/125
5,862,515 A 1/1999 Kobayashi et al. ............ 702/63
5,865,638 A 2/1999 Trafton ....................... 439/288
5,871,858 A 2/1999 Thomsen et al. ............... 429/7
5,872,443 A 2/1999 Williamson ................. 320/160
5,872,453 A 2/1999 Shimoyama et al. ......... 324/431
5,883,306 A 3/1999 Hwang ...................... 73/146.8
5,895,440 A 4/1999 Proctor et al. ................. 702/63
5,903,154 A 5/1999 Zhang et al. ................ 324/437
5,903,716 A 5/1999 Kimber et al. .............. 395/114
5,912,534 A 6/1999 Benedict ...................... 315/82

| | | | | | |
|---|---|---|---|---|---|
| 5,914,605 | A | | 6/1999 | Bertness | 324/430 |
| 5,927,938 | A | | 7/1999 | Hammerslag | 414/809 |
| 5,929,609 | A | | 7/1999 | Joy et al. | 322/25 |
| 5,939,855 | A | | 8/1999 | Proctor et al. | 320/104 |
| 5,939,861 | A | | 8/1999 | Joko et al. | 320/122 |
| 5,945,829 | A | | 8/1999 | Bertness | 324/430 |
| 5,946,605 | A | | 8/1999 | Takahisa et al. | 455/68 |
| 5,951,229 | A | | 9/1999 | Hammerslag | 414/398 |
| 5,955,951 | A | * | 9/1999 | Wischerop et al. | 340/572.8 |
| 5,961,561 | A | | 10/1999 | Wakefield, II | 701/29 |
| 5,961,604 | A | | 10/1999 | Anderson et al. | 709/229 |
| 5,969,625 | A | | 10/1999 | Russo | 340/636.19 |
| 5,973,598 | A | | 10/1999 | Beigel | 340/572.1 |
| 5,978,805 | A | | 11/1999 | Carson | 707/10 |
| 5,982,138 | A | | 11/1999 | Krieger | 320/105 |
| 6,002,238 | A | | 12/1999 | Champlin | 320/134 |
| 6,005,489 | A | * | 12/1999 | Siegle et al. | 340/825.69 |
| 6,005,759 | A | | 12/1999 | Hart et al. | 361/66 |
| 6,008,652 | A | | 12/1999 | Theofanopoulos et al. | 324/434 |
| 6,009,369 | A | | 12/1999 | Boisvert et al. | 701/99 |
| 6,016,047 | A | | 1/2000 | Notten et al. | 320/137 |
| 6,031,354 | A | | 2/2000 | Wiley et al. | 320/116 |
| 6,031,368 | A | | 2/2000 | Klippel et al. | 324/133 |
| 6,037,745 | A | | 3/2000 | Koike et al. | 320/104 |
| 6,037,749 | A | | 3/2000 | Parsonage | 320/132 |
| 6,037,751 | A | | 3/2000 | Klang | 320/160 |
| 6,037,777 | A | | 3/2000 | Champlin | 324/430 |
| 6,037,778 | A | | 3/2000 | Makhija | 324/433 |
| 6,046,514 | A | | 4/2000 | Rouillard et al. | 307/77 |
| 6,051,976 | A | | 4/2000 | Bertness | 324/426 |
| 6,055,468 | A | | 4/2000 | Kaman et al. | 701/29 |
| 6,061,638 | A | | 5/2000 | Joyce | 702/63 |
| 6,064,372 | A | | 5/2000 | Kahkoska | 345/173 |
| 6,072,299 | A | | 6/2000 | Kurle et al. | 320/112 |
| 6,072,300 | A | | 6/2000 | Tsuji | 320/116 |
| 6,081,098 | A | | 6/2000 | Bertness et al. | 320/134 |
| 6,081,109 | A | | 6/2000 | Seymour et al. | 324/127 |
| 6,087,815 | A | | 7/2000 | Pfeifer et al. | 323/282 |
| 6,091,238 | A | | 7/2000 | McDermott | 324/207.2 |
| 6,091,245 | A | | 7/2000 | Bertness | 324/426 |
| 6,094,033 | A | | 7/2000 | Ding et al. | 320/132 |
| 6,100,670 | A | | 8/2000 | Levesque | 320/150 |
| 6,104,167 | A | | 8/2000 | Bertness et al. | 320/132 |
| 6,113,262 | A | | 9/2000 | Purola et al. | 374/45 |
| 6,114,834 | A | | 9/2000 | Parise | 320/109 |
| 6,137,269 | A | | 10/2000 | Champlin | 320/150 |
| 6,140,797 | A | | 10/2000 | Dunn | 320/105 |
| 6,144,185 | A | | 11/2000 | Dougherty et al. | 320/132 |
| 6,147,598 | A | * | 11/2000 | Murphy et al. | 340/426.19 |
| 6,150,793 | A | | 11/2000 | Lesesky et al. | 320/104 |
| 6,158,000 | A | | 12/2000 | Collins | 713/1 |
| 6,161,640 | A | | 12/2000 | Yamaguchi | 180/65.8 |
| 6,163,156 | A | | 12/2000 | Bertness | 324/426 |
| 6,164,063 | A | | 12/2000 | Mendler | 60/274 |
| 6,167,349 | A | | 12/2000 | Alvarez | 702/63 |
| 6,172,483 | B1 | | 1/2001 | Champlin | 320/134 |
| 6,172,505 | B1 | | 1/2001 | Bertness | 324/430 |
| 6,177,737 | B1 | | 1/2001 | Palfey et al. | 307/64 |
| 6,181,545 | B1 | | 1/2001 | Amatucci et al. | 361/502 |
| 6,211,651 | B1 | | 4/2001 | Nemoto | 320/133 |
| 6,215,275 | B1 | | 4/2001 | Bean | 320/106 |
| 6,218,936 | B1 | | 4/2001 | Imao | 340/447 |
| 6,222,342 | B1 | | 4/2001 | Eggert et al. | 320/105 |
| 6,222,369 | B1 | | 4/2001 | Champlin | 324/430 |
| D442,503 | S | | 5/2001 | Lundbeck et al. | D10/77 |
| 6,225,808 | B1 | | 5/2001 | Varghese et al. | 324/426 |
| 6,236,332 | B1 | | 5/2001 | Conkright et al. | 340/3.1 |
| 6,238,253 | B1 | | 5/2001 | Qualls | 439/759 |
| 6,242,887 | B1 | | 6/2001 | Burke | 320/104 |
| 6,249,124 | B1 | | 6/2001 | Bertness | 324/426 |
| 6,250,973 | B1 | | 6/2001 | Lowery et al. | 439/763 |
| 6,254,438 | B1 | | 7/2001 | Gaunt | 439/755 |
| 6,259,170 | B1 | | 7/2001 | Limoge et al. | 307/10.8 |
| 6,259,254 | B1 | | 7/2001 | Klang | 324/427 |
| 6,262,563 | B1 | | 7/2001 | Champlin | 320/134 |
| 6,263,268 | B1 | | 7/2001 | Nathanson | 701/29 |
| 6,271,643 | B1 | | 8/2001 | Becker et al. | 320/112 |
| 6,271,748 | B1 | | 8/2001 | Derbyshire et al. | 340/442 |
| 6,275,008 | B1 | | 8/2001 | Arai et al. | 320/132 |
| 6,294,896 | B1 | | 9/2001 | Champlin | 320/134 |
| 6,294,897 | B1 | | 9/2001 | Champlin | 320/153 |
| 6,304,087 | B1 | | 10/2001 | Bertness | 324/426 |
| 6,307,349 | B1 | | 10/2001 | Koenck et al. | 320/112 |
| 6,310,481 | B2 | | 10/2001 | Bertness | 324/430 |
| 6,313,607 | B1 | | 11/2001 | Champlin | 320/132 |
| 6,313,608 | B1 | | 11/2001 | Varghese et al. | 320/132 |
| 6,316,914 | B1 | | 11/2001 | Bertness | 320/134 |
| 6,320,351 | B1 | | 11/2001 | Ng et al. | 320/104 |
| 6,323,650 | B1 | | 11/2001 | Bertness et al. | 324/426 |
| 6,329,793 | B1 | | 12/2001 | Bertness et al. | 320/132 |
| 6,331,762 | B1 | | 12/2001 | Bertness | 320/134 |
| 6,332,113 | B1 | | 12/2001 | Bertness | 702/63 |
| 6,346,795 | B2 | | 2/2002 | Haraguchi et al. | 320/136 |
| 6,347,958 | B1 | | 2/2002 | Tsai | 439/488 |
| 6,351,102 | B1 | | 2/2002 | Troy | 320/139 |
| 6,356,042 | B1 | | 3/2002 | Kahlon et al. | 318/138 |
| 6,359,441 | B1 | | 3/2002 | Bertness | 324/426 |
| 6,359,442 | B1 | | 3/2002 | Henningson et al. | 324/426 |
| 6,363,303 | B1 | | 3/2002 | Bertness | 701/29 |
| RE37,677 | E | | 4/2002 | Irie | 315/83 |
| 6,377,031 | B1 | | 4/2002 | Karuppana et al. | 323/220 |
| 6,384,608 | B1 | | 5/2002 | Namaky | 324/430 |
| 6,388,448 | B1 | | 5/2002 | Cervas | 324/426 |
| 6,392,414 | B2 | | 5/2002 | Bertness | 324/429 |
| 6,396,278 | B1 | | 5/2002 | Makhija | 324/402 |
| 6,407,554 | B1 | | 6/2002 | Godau et al. | 324/503 |
| 6,411,098 | B1 | | 6/2002 | Laletin | 324/436 |
| 6,417,669 | B1 | | 7/2002 | Champlin | 324/426 |
| 6,420,852 | B1 | | 7/2002 | Sato | 320/134 |
| 6,424,157 | B1 | | 7/2002 | Gollomp et al. | 324/430 |
| 6,424,158 | B2 | | 7/2002 | Klang | 324/433 |
| 6,437,957 | B1 | | 8/2002 | Karuppana et al. | 361/78 |
| 6,441,585 | B1 | | 8/2002 | Bertness | 320/132 |
| 6,445,158 | B1 | | 9/2002 | Bertness et al. | 320/104 |
| 6,449,726 | B1 | | 9/2002 | Smith | 713/340 |
| 6,456,036 | B1 | | 9/2002 | Thandiwe | 320/106 |
| 6,456,045 | B1 | | 9/2002 | Troy et al. | 320/139 |
| 6,465,908 | B1 | | 10/2002 | Karuppana et al. | 307/31 |
| 6,466,025 | B1 | | 10/2002 | Klang | 324/429 |
| 6,466,026 | B1 | | 10/2002 | Champlin | 324/430 |
| 6,469,511 | B1 | | 10/2002 | Vonderhaar et al. | 324/425 |
| 6,477,478 | B1 | | 11/2002 | Jones et al. | 702/102 |
| 6,495,990 | B2 | | 12/2002 | Champlin | 320/132 |
| 6,497,209 | B1 | | 12/2002 | Karuppana et al. | 123/179.3 |
| 6,505,507 | B1 | | 1/2003 | Imao | 73/146.5 |
| 6,507,196 | B2 | | 1/2003 | Thomsen et al. | 324/436 |
| 6,526,361 | B1 | | 2/2003 | Jones et al. | 702/63 |
| 6,529,723 | B1 | | 3/2003 | Bentley | 455/405 |
| 6,531,848 | B1 | | 3/2003 | Chitsazan et al. | 320/153 |
| 6,532,425 | B1 | | 3/2003 | Boost et al. | 702/63 |
| 6,534,992 | B2 | | 3/2003 | Meissner et al. | 324/426 |
| 6,534,993 | B2 | | 3/2003 | Bertness | 324/433 |
| 6,536,536 | B1 | * | 3/2003 | Gass et al. | 173/2 |
| 6,544,078 | B2 | | 4/2003 | Palmisano et al. | 439/762 |
| 6,545,599 | B2 | | 4/2003 | Derbyshire et al. | 340/442 |
| 6,556,019 | B2 | | 4/2003 | Bertness | 324/426 |
| 6,566,883 | B1 | | 5/2003 | Vonderhaar et al. | 324/426 |
| 6,570,385 | B1 | | 5/2003 | Roberts et al. | 324/378 |
| 6,577,107 | B2 | | 6/2003 | Kechmire | 320/139 |
| 6,586,941 | B2 | | 7/2003 | Bertness et al. | 324/426 |
| 6,597,150 | B1 | | 7/2003 | Bertness et al. | 320/104 |
| 6,599,243 | B2 | | 7/2003 | Woltermann et al. | 600/300 |
| 6,600,815 | B1 | | 7/2003 | Walding | 379/93.07 |
| 6,611,740 | B2 | | 8/2003 | Lowrey et al. | 701/29 |
| 6,614,349 | B1 | * | 9/2003 | Proctor et al. | 340/572.1 |
| 6,618,644 | B2 | | 9/2003 | Bean | 700/231 |

6,621,272 B2 9/2003 Champlin ................... 324/426
6,623,314 B1 9/2003 Cox et al. ................... 439/759
6,624,635 B1 9/2003 Lui ........................... 324/426
6,628,011 B2 9/2003 Droppo et al. ................ 307/43
6,629,054 B2 9/2003 Makhija et al. ............. 702/113
6,633,165 B2 10/2003 Bertness ..................... 324/426
6,635,974 B1 10/2003 Karuppana et al. .......... 307/140
6,667,624 B1 12/2003 Raichle et al. .............. 324/522
6,679,212 B2 1/2004 Kelling .................. 123/179.28
6,686,542 B2 2/2004 Zhang ......................... 174/74
6,696,819 B2 2/2004 Bertness ..................... 320/134
6,707,303 B2 3/2004 Bertness et al. ............. 324/426
6,736,941 B2 5/2004 Oku et al. ..................... 203/68
6,737,831 B2 5/2004 Champlin ................... 320/132
6,738,697 B2 5/2004 Breed .......................... 701/29
6,740,990 B2 5/2004 Tozuka et al. ................ 307/9.1
6,745,153 B2 6/2004 White et al. ................ 702/184
7,744,149 6/2004 Karuppana et al. ............ 307/31
6,759,849 B2 7/2004 Bertness ..................... 324/426
6,777,945 B2 8/2004 Roberts et al. .............. 324/426
6,781,382 B2 8/2004 Johnson ...................... 324/426
6,784,635 B2 8/2004 Larson ....................... 320/104
6,784,637 B2 8/2004 Raichle et al. .............. 320/107
6,788,025 B2 9/2004 Bertness et al. ............. 320/104
6,795,782 B2 9/2004 Bertness et al. ............... 702/63
6,796,841 B1 9/2004 Cheng et al. ............. 439/620.3
6,805,090 B2 10/2004 Bertness et al. ............. 123/198
6,806,716 B2 10/2004 Bertness et al. ............. 324/426
6,825,669 B2 11/2004 Raichle et al. .............. 324/426
6,842,707 B2 1/2005 Raichle et al. ................ 702/62
6,845,279 B1* 1/2005 Gilmore et al. ............. 700/115
6,850,037 B2 2/2005 Bertness ..................... 320/132
6,871,151 B2 3/2005 Bertness ....................... 702/63
6,885,195 B2 4/2005 Bertness ..................... 324/426
6,888,468 B2 5/2005 Bertness ................ 340/636.15
6,891,378 B2 5/2005 Bertness et al. ............. 324/426
6,904,796 B2 6/2005 Pacsai et al. ............... 73/146.8
6,906,522 B2 6/2005 Bertness et al. ............. 324/426
6,906,523 B2 6/2005 Bertness et al. ............. 324/426
6,906,624 B2 6/2005 McClelland et al. ........ 340/442
6,909,287 B2 6/2005 Bertness ..................... 324/427
6,913,483 B2 7/2005 Restaino et al. ............ 439/504
6,914,413 B2 7/2005 Bertness et al. ............. 320/104
6,919,725 B2 7/2005 Bertness et al. ............. 324/433
6,930,485 B2 8/2005 Bertness et al. ............. 324/426
6,933,727 B2 8/2005 Bertness et al. ............. 324/426
6,941,234 B2 9/2005 Bertness et al. ............... 702/63
6,967,484 B2 11/2005 Bertness ..................... 324/426
6,972,662 B1 12/2005 Ohkawa et al. ............ 340/10.1
6,998,847 B2 2/2006 Bertness et al. ............. 324/426
7,003,410 B2 2/2006 Bertness et al. ............... 702/63
7,003,411 B2 2/2006 Bertness ....................... 702/63
7,012,433 B2 3/2006 Smith et al. ................. 324/426
7,058,525 B2 6/2006 Bertness et al. ............... 702/63
7,081,755 B2 7/2006 Klang et al. ................ 324/426
7,106,070 B2 9/2006 Bertness et al. ............. 324/538
7,116,109 B2 10/2006 Klang ........................ 324/426
7,119,686 B2 10/2006 Bertness et al. .......... 340/572.1
7,126,341 B2 10/2006 Bertness et al. ............. 324/426
7,129,706 B2 10/2006 Kalley ........................ 324/426
7,184,905 B2 2/2007 Stefan .......................... 702/63
7,200,424 B2 4/2007 Tischer et al. ............... 455/567
7,235,977 B2 6/2007 Koran et al. ................ 324/426
7,272,519 B2 9/2007 Lesesky et al. ................ 702/63
7,446,536 B2 11/2008 Bertness ..................... 324/426
2002/0004694 A1 1/2002 Mcleod ........................ 701/29
2002/0010558 A1 1/2002 Bertness et al. ............... 702/63
2002/0041175 A1 4/2002 Lauper et al. ............... 320/106
2002/0044050 A1 4/2002 Derbyshire et al. ......... 340/442
2002/0118111 A1* 8/2002 Brown et al. ............. 340/573.1
2002/0171428 A1 11/2002 Bertness ....................... 702/63
2002/0176010 A1 11/2002 Wallach et al. .............. 348/362
2003/0009270 A1 1/2003 Breed .......................... 701/29
2003/0025481 A1 2/2003 Bertness ..................... 324/427
2003/0036909 A1 2/2003 Kato .......................... 704/275
2003/0040873 A1 2/2003 Lesesky et al. ................ 702/57
2003/0088375 A1 5/2003 Bertness et al. ............... 702/63
2003/0137277 A1 7/2003 Mori et al. .................. 320/132
2003/0169018 A1 9/2003 Berels et al. ................ 320/132
2003/0184262 A1 10/2003 Makhija ..................... 320/156
2003/0184306 A1 10/2003 Bertness et al. ............. 324/426
2003/0187556 A1 10/2003 Suzuki ........................ 701/29
2003/0194672 A1 10/2003 Roberts et al. .............. 431/196
2003/0212311 A1* 11/2003 Nova et al. .................. 600/300
2003/0214395 A1 11/2003 Flowerday et al. .......... 340/445
2004/0000590 A1 1/2004 Raichle et al. ......... 235/462.01
2004/0000891 A1 1/2004 Raichle et al. .............. 320/107
2004/0000893 A1 1/2004 Raichle et al. .............. 320/135
2004/0002824 A1 1/2004 Raichle et al. ................ 702/63
2004/0002825 A1 1/2004 Raichle et al. ................ 702/63
2004/0002836 A1 1/2004 Raichle et al. .............. 702/188
2004/0032264 A1 2/2004 Schoch ....................... 324/426
2004/0044452 A1 3/2004 Bauer et al. .................... 703/33
2004/0049361 A1 3/2004 Hamdan et al. ............. 702/115
2004/0051533 A1 3/2004 Namaky ..................... 324/426
2004/0054503 A1 3/2004 Namaky ..................... 702/182
2004/0113588 A1 6/2004 Mikuriya et al. ............ 320/128
2004/0145342 A1 7/2004 Lyon .......................... 320/108
2004/0178185 A1 9/2004 Yoshikawa et al. .......... 219/270
2004/0199343 A1 10/2004 Cardinal et al. ............... 702/63
2004/0227523 A1 11/2004 Namaky ..................... 324/537
2004/0239332 A1 12/2004 Mackel et al. ............... 324/426
2005/0017726 A1 1/2005 Koran et al. ................ 324/433
2005/0021294 A1* 1/2005 Trsar et al. .................. 702/183
2005/0025299 A1* 2/2005 Tischer et al. ............... 379/199
2005/0043868 A1 2/2005 Mitcham ..................... 701/29
2005/0057256 A1 3/2005 Bertness ..................... 324/426
2005/0102073 A1 5/2005 Ingram ........................ 701/29
2005/0128083 A1* 6/2005 Puzio et al. .............. 340/572.1
2005/0159847 A1* 7/2005 Shah et al. .................. 700/276
2005/0173142 A1* 8/2005 Cutler et al. ................ 173/181
2005/0182536 A1 8/2005 Doyle et al. .................. 701/29
2005/0254106 A9 11/2005 Silverbrook et al. ........ 358/539
2005/0256617 A1 11/2005 Cawthorne et al. ............ 701/22
2006/0030980 A1 2/2006 St. Denis ..................... 701/29
2006/0089767 A1 4/2006 Sowa .......................... 701/29
2006/0217914 A1 9/2006 Bertness ..................... 702/113
2006/0282323 A1 12/2006 Walker et al. ................. 705/14
2007/0026916 A1 2/2007 Juds et al. ...................... 463/1

FOREIGN PATENT DOCUMENTS

EP 0 022 450 A1 1/1981
EP 0 637 754 A1 2/1995
EP 0 982 159 A2 3/2000
FR 2 749 397 12/1997
GB 2 029 586 3/1980
GB 2 088 159 A 6/1982
GB 2 246 916 A 10/1990
GB 2 275 783 A 7/1994
GB 2 387 235 A 10/2003
JP 59-17892 1/1984
JP 59-17893 1/1984
JP 59-17894 1/1984
JP 59017894 1/1984
JP 59215674 12/1984
JP 60225078 11/1985
JP 62-180284 8/1987
JP 63027776 2/1988
JP 03274479 12/1991
JP 03282276 12/1991
JP 4-8636 1/1992
JP 04095788 3/1992
JP 04131779 5/1992
JP 04372536 12/1992
JP 05211724 A 8/1993

| | | | |
|---|---|---|---|
| JP | 5216550 | | 8/1993 |
| JP | 7-128414 | | 5/1995 |
| JP | 09061505 | | 3/1997 |
| JP | 10056744 | | 2/1998 |
| JP | 10232273 | | 9/1998 |
| JP | 11103503 | A | 4/1999 |
| RU | 2089015 | C1 | 8/1997 |
| WO | WO 93/22666 | | 11/1993 |
| WO | WO 94/05069 | | 3/1994 |
| WO | WO 96/01456 | | 1/1996 |
| WO | WO 96/06747 | | 3/1996 |
| WO | WO 97/01103 | | 1/1997 |
| WO | WO 97/44652 | | 11/1997 |
| WO | WO 98/04910 | | 2/1998 |
| WO | WO 98/58270 | | 12/1998 |
| WO | WO 99/23738 | | 5/1999 |
| WO | WO 00/16083 | | 3/2000 |
| WO | WO 00/62049 | | 10/2000 |
| WO | WO 00/67359 | | 11/2000 |
| WO | WO 01/59443 | | 2/2001 |
| WO | WO 01/16614 | | 3/2001 |
| WO | WO 01/16615 | | 3/2001 |
| WO | WO 01/51947 | | 7/2001 |
| WO | WO 03/047064 | A3 | 6/2003 |
| WO | WO 03/076960 | A1 | 9/2003 |
| WO | WO 2004/047215 | A1 | 6/2004 |

OTHER PUBLICATIONS

"Battery Impedance", by E. Willihnganz et al., *Electrical Engineering*, Sep. 1959, pp. 922-925.

"Determining The End of Battery Life", by S. DeBardelaben, *IEEE*, 1986, pp. 365-368.

"A Look at the Impedance of a Cell", by S. Debardelaben, *IEEE*, 1988, pp. 394-397.

"The Impedance of Electrical Storage Cells", by N. A. Hampson et al., *Journal of Applied Electrochemistry*, 1980, pp. 3-11.

"A Package for Impedance/Admittance Data Analysis", by B. Boukamp, *Solid State Ionics*, 1986, pp. 136-140.

"Precision of Impedance Spectroscopy Estimates of Bulk, Reaction Rate, and Diffusion Parameters", by J. Macdonald et al., *J. Electroanal, Chem*., 1991, pp. 1-11.

37 Internal Resistance: Harbinger of Capacity Loss in Starved Electrolyte Sealed Lead Acid Batteries, by Vaccaro, F.J. et al., *AT&T Bell Laboratories*, 1987 IEEE, Ch. 2477, pp. 128,131.

IEEE Recommended Practice for Maintenance, Testings, and Replacement of Large Lead Storage Batteries for Generating Stations and Substations, *The Institute of Electrical and Electronics Engineers, Inc., ANSI/IEEE Std*. 450-1987, Mar. 9, 1987, pp. 7-15.

"Field and Laboratory Studies to Assess the State of Health of Valve-Regulated Lead Acid Batteries: Part I Conductance/Capacity Correlation Studies", by D. Feder et al., *IEEE*, Aug. 1992, pp. 218-233.

"JIS Japanese Industrial Standard-Lead Acid Batteries for Automobiles", *Japanese Standards Association UDC*, 621.355.2:629.113.006, Nov. 1995.

"Performance of Dry Cells", by C. Hambuechen, Preprint of *Am. Electrochem. Soc*., Apr. 18-20, 1912, paper No. 19, pp. 1-5.

"A Bridge for Measuring Storage Battery Resistance", by E. Willihncanz, *The Electrochemical Society*, preprint 79-20, Apr. 1941, pp. 253-258.

National Semiconductor Corporation, "High Q Notch Filter", 3/69, Linear Brief 5, Mar. 1969.

Burr-Brown Corporation, "Design a 60 Hz Notch Filter with the UAF42", 1/94, AB-071, 1994.

National Semiconductor Corporation, "LMF90-4$^{th}$-Order Elliptic Notch Filter", 12/94, RRD-B30M115, Dec. 1994.

"Alligator Clips with Wire Penetrators" *J.S. Popper, Inc*. product information, downloaded from http://www.jspopper.com/, undated.

"#12: LM78S40 Simple Switcher DC to DC Converter", *ITM e-Catalog*, downloaded from http://www.pcbcafe.com, undated.

"Simple DC-DC Converts Allows Use of Single Battery", *Electronix Express*, downloaded from http://www.elexp.com/t_dc-dc.htm, undated.

"DC-DC Converter Basics", *Power Designers*, downloaded from http://www.powederdesigners.com/InforWeb.design_center/articles/DC-DC/converter.shtm, undated.

"Notification of Transmittal of The International Search Report or the Declaration", PCT/US02/29461.

"Notification of Transmittal of The International Search Report or the Declaration", PCT/US03/07546.

"Notification of Transmittal of The International Search Report or the Declaration", PCT/US03/06577.

"Notification of Transmittal of The International Search Report or the Declaration", PCT/US03/07837.

"Improved Impedance Spectroscopy Technique for Status Determination of Production Li/$SO_2$ Batteries" Terrill Atwater et al., pp. 10-113, (1992).

"Notification of Transmittal of The International Search Report or the Declaration", PCT/US03/41561.

"Notification of Transmittal of The International Search Report or the Declaration", PCT/US03/27696.

"Programming Training Course, 62-000 Series Smart Engine Analyzer", Testproducts Division, Kalamazoo, Michigan, pp. 1-207, (1984).

"Operators Manual, Modular Computer Analyzer Model MCA 3000", Sun Electric Corporation, Crystal Lake, Illinois, pp. 1-1-14-13, (1991).

"Dynamic modelling of lead/acid batteries using impedance spectroscopy for parameter identification", Journal of Power Sources, pp. 69-84, (1997).

Notification of Transmittal of the International Search Report for PCT/US03/30707.

"A review of impedance measurements for determination of the state-of-charge or state-of-health of secondary batteries", Journal of Power Sources, pp. 59-69, (1998).

"Search Report Under Section 17" for Great Britain Application No. GB0421447.4.

"Results of Discrete Frequency Immittance Spectroscopy (DFIS) Measurements of Lead Acid Batteries", by K.S. Champlin et al., *Proceedings of 23$^{rd}$ International Teleco Conference* (*INTELEC*), published Oct. 2001, IEE, pp. 433-440.

"Examination Report" from the U.K. Patent Office for U.K. App. No. 0417678.0.

"Professional BCS System Analyzer Battery-Charger-Starting", pp. 2-8, (2001).

Young Illustrated Encyclopedia Dictionary of Electronics, 1981, Parker Publishing Company, Inc., pp. 318-319.

"DSP Applications in Hybrid Electric Vehicle Powertrain", Miller et al., Proceedings of the American Control Conference, Sand Diego, CA, Jun. 1999; 2 ppg.

"Notification of Transmittal of the International Search Report and the Written Opinion of the International Searching Authority, or the Declaration" for PCT/US2008/008702 filed Jul. 2008; 15 pages.

"Notification Concerning Availability of the Publication of the International Application" for PCT/US2008/008702, filed Jul. 17, 2008; 24 pages.

"A Microprocessor-Based Control System for a Near-Term Electric Vehicle", Bimal K. Bose; IEEE Transactions on Industry Applications, vol. IA-17, No. 6, Nov./Dec. 198?,; 0093-9994/81/1100-0626$00.75 © 1981 IEEE, 6 pages.

"First Notice Informing the Applicant of the Communication of the International Application (To Designated Offices which do not apply the 30 Month Time Limit Under Article 22(1))" for PCT/US2008/008702 filed Jul. 17, 2008; one page.

"Notification of the Recording of a Change" for PCT/US2008/008702 filed Jul. 17, 2008; one page.

* cited by examiner

THEFT PREVENTION DEVICE FOR AUTOMOTIVE VEHICLE SERVICE CENTERS

The present application claims the benefit of U.S. provisional patent application Ser. No. 60/705,389, filed Aug. 4, 2005 and is a continuation-in-part of U.S. patent application Ser. No. 10/823,140, filed Apr. 13, 2004, entitled "THEFT PREVENTION DEVICE FOR AUTOMOTIVE VEHICLE SERVICE CENTERS," the contents of which are hereby incorporated by reference in their entirety.

BACKGROUND OF THE INVENTION

The present invention relates to portable tools of the type used in automotive vehicle service centers. More specifically, the present invention relates to a theft prevention device used to prevent theft of portable tools from the automotive vehicle service centers.

Portable tools in automotive service centers have a variety of applications. Some portable tools can be used to test various components of an automobile such that problems associated with the automobile can be diagnosed. For example, storage batteries used in automotive vehicles, both electrical vehicles and vehicles with internal combustion engines, as well as power supplies such as backup power systems are often tested in an automotive service center. It is desirable to measure the condition of such storage batteries with a portable battery tester. For example, it can be useful to determine the amount of charge a storage battery can hold (i.e. the capacity of the battery) or the state of health of a storage battery.

A number of battery testing techniques are known in the art. These techniques include measuring the specific gravity of acid contained in a storage battery. Measuring a battery voltage and performing a load test on a battery in which a large load is placed on the battery and the response observed. More recently, a technique has been pioneered by Dr. Keith S. Champlin and Midtronics, Inc. of Willowbrook, Ill. for testing storage batteries by measuring the conductance of the batteries. This technique is described in a number of United State patents, for example, U.S. Pat. No. 3,873,911, issued Mar. 25, 1975, to Champlin, entitled ELECTRONIC BATTERY TESTING DEVICE; U.S. Pat. No. 3,909,708, issued Sep. 30, 1975, to Champlin, entitled ELECTRONIC BATTERY TESTING DEVICE; U.S. Pat. No. 4,816,768, issued Mar. 28, 1989, to Champlin, entitled ELECTRONIC BATTERY TESTING DEVICE; U.S. Pat. No. 4,825,170, issued Apr. 25, 1989, to Champlin, entitled ELECTRONIC BATTERY TESTING DEVICE WITH AUTOMATIC VOLTAGE SCALING; U.S. Pat. No. 4,881,038, issued Nov. 14, 1989, to Champlin, entitled ELECTRONIC BATTERY TESTING DEVICE WITH AUTOMATIC VOLTAGE SCALING TO DETERMINE DYNAMIC CONDUCTANCE; U.S. Pat. No. 4,912,416, issued Mar. 27, 1990, to Champlin, entitled ELECTRONIC BATTERY TESTING DEVICE WITH STATE-OF-CHARGE COMPENSATION; U.S. Pat. No. 5,140,269, issued Aug. 18, 1992, to Champlin, entitled ELECTRONIC TESTER FOR ASSESSING BATTERY/CELL CAPACITY; U.S. Pat. No. 5,343,380, issued Aug. 30, 1994, entitled METHOD AND APPARATUS FOR SUPPRESSING TIME-VARYING SIGNALS IN BATTERIES UNDERGOING CHARGING OR DISCHARGING; U.S. Pat. No. 5,572,136, issued Nov. 5, 1996, entitled ELECTRONIC BATTERY TESTER DEVICE; U.S. Pat. No. 5,574,355, issued Nov. 12, 1996, entitled METHOD AND APPARATUS FOR DETECTION AND CONTROL OF THERMAL RUNAWAY IN A BATTERY UNDER CHARGE; U.S. Pat. No. 5,585,416, issued Dec. 10, 1996, entitled APPARATUS AND METHOD FOR STEP-CHARGING BATTERIES TO OPTIMIZE CHARGE ACCEPTANCE; U.S. Pat. No. 5,585,728, issued Dec. 17, 1996, entitled ELECTRONIC BATTERY TESTER WITH AUTOMATIC COMPENSATION FOR LOW STATE-OF-CHARGE; U.S. Pat. No. 5,589,757, issued Dec. 31, 1996, entitled APPARATUS AND METHOD FOR STEP-CHARGING BATTERIES TO OPTIMIZE CHARGE ACCEPTANCE; U.S. Pat. No. 5,592,093, issued Jan. 7, 1997, entitled. ELECTRONIC. BATTERY TESTING DEVICE LOOSE TERMINAL CONNECTION DETECTION VIA A COMPARISON CIRCUIT; U.S. Pat. No. 5,598,098, issued Jan. 28, 1997, entitled ELECTRONIC BATTERY TESTER WITH VERY HIGH NOISE IMMUNITY; U.S. Pat. No. 5,656,920, issued Aug. 12, 1997, entitled METHOD FOR OPTIMIZING THE CHARGING LEAD-ACID BATTERIES AND AN INTERACTIVE CHARGER; U.S. Pat. No. 5,757,192, issued May 26, 1998, entitled METHOD AND APPARATUS FOR DETECTING A BAD CELL IN A STORAGE BATTERY; U.S. Pat. No. 5,821,756, issued Oct. 13, 1998, entitled ELECTRONIC BATTERY TESTER WITH TAILORED COMPENSATION FOR LOW STATE-OF CHARGE; U.S. Pat. No. 5,831,435, issued Nov. 3, 1998, entitled BATTERY TESTER FOR JIS STANDARD; U.S. Pat. No. 5,871,858, issued Feb. 16, 1999, entitled ANTI-THEFT BATTERY; U.S. Pat. No. 5,914,605, issued Jun. 22, 1999, entitled ELECTRONIC BATTERY TESTER; U.S. Pat. No. 5,945,829, issued Aug. 31, 1999, entitled MIDPOINT BATTERY MONITORING; U.S. Pat. No. 6,002,238, issued Dec. 14, 1999, entitled METHOD AND APPARATUS FOR MEASURING COMPLEX IMPEDANCE OF CELLS AND BATTERIES; U.S. Pat. No. 6,037,751, issued Mar. 14, 2000, entitled APPARATUS FOR CHARGING BATTERIES; U.S. Pat. No. 6,037,777, issued Mar. 14, 2000, entitled METHOD AND APPARATUS FOR DETERMINING BATTERY PROPERTIES FROM COMPLEX IMPEDANCE/ADMITTANCE; U.S. Pat. No. 6,051,976, issued Apr. 18, 2000, entitled METHOD AND APPARATUS FOR AUDITING A BATTERY TEST; U.S. Pat. No. 6,081,098, issued Jun. 27, 2000, entitled METHOD AND APPARATUS FOR CHARGING A BATTERY; U.S. Pat. No. 6,091,245, issued Jul. 18, 2000, entitled METHOD AND APPARATUS FOR AUDITING A BATTERY TEST; U.S. Pat. No. 6,104,167, issued Aug. 15, 2000, entitled METHOD AND APPARATUS FOR CHARGING A BATTERY; U.S. Pat. No. 6,137,269, issued Oct. 24, 2000, entitled METHOD AND APPARATUS FOR ELECTRONICALLY EVALUATING THE INTERNAL TEMPERATURE OF AN ELECTROCHEMICAL CELL OR BATTERY; U.S. Pat. No. 6,163,156, issued Dec. 19, 2000, entitled ELECTRICAL CONNECTION FOR ELECTRONIC BATTERY TESTER; U.S. Pat. No. 6,172,483, issued Jan. 9, 2001, entitled METHOD AND APPARATUS FOR MEASURING COMPLEX IMPEDANCE OF CELLS AND BATTERIES; U.S. Pat. No. 6,172,505, issued Jan. 9, 2001, entitled ELECTRONIC BATTERY TESTER; U.S. Pat. No. 6,222,369, issued Apr. 24, 2001, entitled METHOD AND APPARATUS FOR DETERMINING BATTERY PROPERTIES FROM COMPLEX IMPEDANCE/ADMITTANCE; U.S. Pat. No. 6,225,808, issued May 1, 2001, entitled TEST COUNTER FOR ELECTRONIC BATTERY TESTER; U.S. Pat. No. 6,249,124, issued Jun. 19, 2001, entitled ELECTRONIC BATTERY TESTER WITH INTERNAL BATTERY; U.S. Pat. No. 6,259,254, issued Jul. 10, 2001, entitled APPARATUS AND METHOD FOR CARRYING OUT DIAGNOSTIC TESTS ON BATTERIES AND FOR RAPIDLY CHARGING BATTERIES; U.S. Pat. No. 6,262,563, issued Jul. 17, 2001, entitled METHOD AND APPARATUS FOR MEASURING COMPLEX ADMITTANCE OF CELLS AND BATTERIES; U.S. Pat. No. 6,294,896, issued Sep. 25, 2001; entitled METHOD AND APPARATUS FOR MEASURING COMPLEX SELF-IMMITANCE OF A GENERAL ELECTRICAL ELEMENT; U.S. Pat. No. 6,294,897, issued Sep. 25, 2001, entitled METHOD AND APPARATUS FOR ELECTRONICALLY EVALUATING THE INTERNAL TEMPERATURE OF AN ELECTROCHEMICAL CELL OR BATTERY; U.S. Pat. No. 6,304,087, issued Oct. 16, 2001, entitled APPARATUS FOR CALIBRATING ELECTRONIC BATTERY TESTER; U.S. Pat. No. 6,310,481, issued Oct. 30, 2001, entitled ELECTRONIC BATTERY TESTER; U.S. Pat. No. 6,313,607, issued Nov. 6, 2001, entitled METHOD AND APPARATUS FOR EVALUATING STORED CHARGE IN AN ELECTROCHEMICAL CELL OR BATTERY; U.S. Pat. No. 6,313,608, issued Nov. 6, 2001, entitled METHOD AND APPARATUS FOR CHARGING A BATTERY; U.S. Pat. No. 6,316,914, issued Nov. 13, 2001, entitled TESTING PARALLEL STRINGS OF STORAGE BATTERIES; U.S. Pat. No. 6,323,650, issued Nov. 27, 2001, entitled ELECTRONIC BATTERY TESTER; U.S. Pat. No. 6,329,793, issued Dec. 11, 2001, entitled METHOD AND APPARATUS FOR CHARGING A BATTERY; U.S. Pat. No. 6,331,762, issued Dec. 18, 2001, entitled ENERGY MANAGEMENT SYSTEM FOR AUTOMOTIVE VEHICLE; U.S. Pat. No. 6,332,113, issued Dec. 18, 2001, entitled ELECTRONIC BATTERY TESTER; U.S. Pat. No. 6,351,102, issued Feb. 26, 2002, entitled AUTOMOTIVE BATTERY CHARGING SYSTEM TESTER; U.S. Pat. No. 6,359,441, issued Mar. 19, 2002, entitled ELECTRONIC BATTERY TESTER; U.S. Pat. No. 6,363,303, issued Mar. 26, 2002, entitled ALTERNATOR DIAGNOSTIC SYSTEM; U.S. Pat. No. 6,377,031, issued Apr. 23, 2002, entitled INTELLIGENT SWITCH FOR POWER MANAGEMENT; U.S. Pat. No. 6,392,414, issued May 21, 2002, entitled ELECTRONIC BATTERY TESTER; U.S. Pat. No. 6,417,669, issued Jul. 9, 2002, entitled SUPPRESSING INTERFERENCE IN AC MEASUREMENTS OF CELLS, BATTERIES AND OTHER ELECTRICAL ELEMENTS; U.S. Pat. No. 6,424,158, issued Jul. 23, 2002, entitled APPARATUS AND METHOD FOR CARRYING OUT DIAGNOSTIC TESTS ON BATTERIES AND FOR RAPIDLY CHARGING BATTERIES; U.S. Pat. No. 6,441,585, issued Aug. 17, 2002, entitled APPARATUS AND METHOD FOR TESTING RECHARGEABLE ENERGY STORAGE BATTERIES; U.S. Pat. No. 6,437,957, issued Aug. 20, 2002, entitled SYSTEM AND METHOD FOR PROVIDING SURGE, SHORT, AND REVERSE POLARITY CONNECTION PROTECTION; U.S. Pat. No. 6,445,158, issued Sep. 3, 2002, entitled VEHICLE ELECTRICAL SYSTEM TESTER WITH ENCODED OUTPUT; U.S. Pat. No. 6,456,045, issued Sep. 24, 2002, entitled INTEGRATED CONDUCTANCE AND LOAD TEST BASED ELECTRONIC BATTERY TESTER; U.S. Pat. No. 6,466,025, issued Oct. 15, 2002, entitled ALTERNATOR TESTER; U.S. Pat. No. 6,465,908, issued Oct. 15, 2002, entitled INTELLIGENT POWER MANAGEMENT SYSTEM; U.S. Pat. No. 6,466,026, issued Oct. 15, 2002, entitled PROGRAMMABLE CURRENT EXCITER FOR MEASURING AC IMMITTANCE OF CELLS AND BATTERIES; U.S. Pat. No. 6,469,511, issued Nov. 22, 2002, entitled BATTERY CLAMP WITH EMBEDDED ENVIRONMENT SENSOR; U.S. Pat. No. 6,495,990, issued Dec. 17, 2002, entitled METHOD AND APPARATUS FOR EVALUATING STORED CHARGE IN AN ELECTROCHEMICAL CELL OR BATTERY; U.S. Pat. No. 6,497,209, issued Dec. 24, 2002, entitled SYSTEM AND METHOD FOR PROTECTING A CRANKING SUBSYSTEM; U.S. Pat. No. 6,507,196, issued Jan. 14, 2003; entitled BATTERY HAVING DISCHARGE STATE INDICATION; U.S. Pat. No. 6,534,993, issued Mar. 18, 2003, entitled ELECTRONIC BATTERY TESTER; U.S. Pat. No. 6,544,078, issued Apr. 8, 2003, entitled BATTERY CLAMP WITH INTEGRATED CURRENT SENSOR; U.S. Pat. No. 6,556,019, issued Apr. 29, 2003, entitled ELECTRONIC BATTERY TESTER; U.S. Pat. No. 6,566,883, issued May 20, 2003, entitled ELECTRONIC BATTERY TESTER; U.S. Pat. No. 6,586,941, issued Jul. 1, 2003, entitled BATTERY TESTER WITH DATABUS; U.S. Pat. No. 6,597,150, issued Jul. 22, 2003, entitled METHOD OF DISTRIBUTING JUMP-START BOOSTER PACKS; U.S. Pat. No. 6,621,272, issued Sep. 16, 2003, entitled PROGRAMMABLE CURRENT EXCITER FOR MEASURING AC IMMITTANCE OF CELLS AND BATTERIES; U.S. Pat. No. 6,623,314, issued Sep. 23, 2003, entitled KELVIN CLAMP FOR ELECTRICALLY COUPLING TO A BATTERY CONTACT; U.S. Pat. No. 6,633,165, issued Oct. 14, 2003, entitled IN-VEHICLE BATTERY MONITOR; U.S. Pat. No. 6,635,974, issued Oct. 21, 2003, entitled SELF-LEARNING POWER MANAGEMENT SYSTEM AND METHOD; U.S. Pat. No. 6,707,303, issued Mar. 16, 2004, entitled ELECTRONIC BATTERY TESTER; U.S. Pat. No. 6,737,831, issued May 18, 2004, entitled METHOD AND APPARATUS USING A CIRCUIT MODEL TO EVALUATE CELL/BATTERY PARAMETERS; U.S. Pat. No. 6,744,149, issued Jun. 1, 2004, entitled SYSTEM AND METHOD FOR PROVIDING STEP-DOWN POWER CONVERSION USING AN INTELLIGENT SWITCH; U.S. Pat. No. 6,759,849, issued Jul. 6, 2004, entitled BATTERY TESTER CONFIGURED TO RECEIVE A REMOVABLE DIGITAL MODULE; U.S. Pat. No. 6,781,382, issued Aug. 24, 2004, entitled ELECTRONIC BATTERY TESTER; U.S. Pat. No. 6,788,025, filed Sep. 7, 2004, entitled BATTERY CHARGER WITH BOOSTER PACK; U.S. Pat. No. 6,795,782, issued Sep. 21, 2004, entitled BATTERY TEST MODULE; U.S. Pat. No. 6,805,090, filed Oct. 19, 2004, entitled CHARGE CONTROL SYSTEM FOR A VEHICLE BATTERY; U.S. Pat. No. 6,806,716, filed Oct. 19, 2004, entitled ELECTRONIC BATTERY TESTER; U.S. Pat. No. 6,850,037, filed Feb. 1, 2005, entitled IN-VEHICLE BATTERY MONITORING; U.S. Pat. No. 6,850,037, issued Feb. 1, 2005, entitled IN-VEHICLE BATTERY MONITOR; U.S. Pat. No. 6,871,151, issued Mar. 22, 2005, entitled ELECTRONIC BATTERY TESTER WITH NETWORK COMMUNICATION; U.S. Pat. No. 6,885,195, issued Apr. 26, 2005, entitled METHOD AND APPARATUS FOR AUDITING A BATTERY TEST; U.S. Pat. No. 6,888,468, issued May 3, 2005, entitled APPARATUS AND METHOD FOR PROTECTING A BATTERY FROM OVERDISCHARGE; U.S. Pat. No. 6,891,378, issued May 10, 2005, entitled ELECTRONIC BATTERY TESTER; U.S. Pat. No. 6,906,522, issued Jun. 14, 2005, entitled BATTERY TESTER WITH BATTERY REPLACEMENT OUTPUT; U.S. Pat. No. 6,906,523, issued Jun. 14, 2005, entitled METHOD AND APPARATUS FOR TESTING CELLS AND BATTERIES EMBEDDED IN SERIES/PARALLEL SYSTEMS; U.S. Pat. No. 6,909,287, issued Jun. 21, 2005, entitled ENERGY MANAGEMENT SYSTEM WITH AUTOMOTIVE VEHICLE; U.S. Pat. No. 6,914,413, issued Jul. 5, 2005, entitled ALTERNATOR TESTER WITH ENCODED OUTPUT; U.S. Pat. No. 6,913,483, issued Jul. 5, 2005, entitled CABLE FOR ELECTRONIC BATTERY TESTER; U.S. Pat. No. 6,930,485, issued Aug. 16, 2005, entitled ELECTRONIC BATTERY TESTER WITH BATTERY FAILURE TEMPERATURE DETERMINATION; U.S. Pat. No. 6,933,727, issued Aug. 23, 2005, entitled ELECTRONIC BATTERY TESTER CABLE, U.S. Pat. No. 6,941,234, filed Sep. 6, 2005, entitled QUERY BASED ELECTRONIC BATTERY TESTER; U.S. Pat. No. 6,967,484, issued Nov. 22, 2005, entitled MODULAR BATTERY TESTER FOR SCAN TOOL; U.S. Ser. No. 09/780,146,filed Feb. 9, 2001, entitled STORAGE BATTERY WITH INTEGRAL BATTERY TESTER; U.S. Ser. No. 09/756,638, filed Jan. 8, 2001, entitled METHOD AND APPARATUS FOR DETERMINING BATTERY PROPERTIES FROM COMPLEX IMPEDANCE/ADMITTANCE; U.S. Ser. No. 09/862,783, filed May 21, 2001, entitled METHOD AND APPARATUS FOR TESTING CELLS AND BATTERIES EMBEDDED IN SERIES/PARALLEL SYSTEMS; U.S. Ser. No. 09/880,473, filed Jun. 13, 2001; entitled BATTERY TEST MODULE; U.S. Ser. No. 09/993,468, filed Nov. 14, 2001, entitled KELVIN CONNECTOR FOR A BATTERY POST; U.S. Ser. No. 10/042,451, filed Jan. 8, 2002, entitled BATTERY CHARGE CONTROL DEVICE; U.S. Ser. No. 10/109,734, filed Mar. 28, 2002, entitled APPARATUS AND METHOD FOR COUNTERACTING SELF DISCHARGE IN A STORAGE BATTERY; U.S. Ser. No. 10/112,998, filed Mar. 29, 2002, entitled BATTERY TESTER WITH BATTERY REPLACEMENT OUTPUT; U.S. Ser. No. 10/200,041, filed Jul. 19, 2002, entitled AUTOMOTIVE VEHICLE ELECTRICAL SYSTEM DIAGNOSTIC DEVICE; U.S. Ser. No. 10/217,913, filed Aug. 13, 2002, entitled, BATTERY TEST MODULE; U.S. Ser. No. 10/246,439, filed Sep. 18, 2002, entitled BATTERY TESTER UPGRADE USING SOFTWARE KEY; U.S. Ser. No. 10/263,473, filed Oct. 2, 2002, entitled ELECTRONIC BATTERY TESTER WITH RELATIVE TEST OUTPUT; U.S. Ser. No. 10/310,385, filed Dec. 5, 2002, entitled BATTERY TEST MODULE; U.S. Ser. No. 10/462,323, filed Jun. 16, 2003, entitled ELECTRONIC BATTERY TESTER HAVING A USER INTERFACE TO CONFIGURE A PRINTER; U.S. Ser. No. 10/653,342, filed Sep. 2, 2003, entitled ELECTRONIC BATTERY TESTER CONFIGURED TO PREDICT A LOAD TEST RESULT; U.S. Ser. No. 10/654,098, filed Sep. 3, 2003, entitled BATTERY TEST OUTPUTS ADJUSTED BASED UPON BATTERY TEMPERATURE AND THE STATE OF DISCHARGE OF THE BATTERY; U.S. Ser. No. 10/656,526, filed Sep. 5, 2003, entitled METHOD AND APPARATUS FOR MEASURING A PARAMETER OF A VEHICLE ELECTRICAL SYSTEM; U.S. Ser. No. 10/441,271, filed May 19, 2003, entitled ELECTRONIC BATTERY TESTER; U.S. Ser. No. 09/653,963, filed Sep. 1, 2000, entitled SYSTEM AND METHOD FOR CONTROLLING POWER GENERATION AND STORAGE; U.S. Ser. No. 10/174,110, filed Jun. 18, 2002, entitled DAYTIME RUNNING LIGHT CONTROL USING AN INTELLIGENT POWER MANAGEMENT SYSTEM; U.S. Ser. No. 10/258,441, filed Apr. 9, 2003, entitled CURRENT MEASURING CIRCUIT SUITED FOR BATTERIES; U.S. Ser. No. 10/705,020, filed Nov. 11, 2003, entitled APPARATUS AND METHOD FOR SIMULATING A BATTERY TESTER WITH A FIXED RESISTANCE LOAD; U.S. Ser. No. 10/681,666, filed Oct. 8, 2003, entitled ELECTRONIC BATTERY TESTER WITH PROBE LIGHT; U.S. Ser. No. 10/748,792, filed Dec. 30, 2003, entitled APPARATUS AND METHOD FOR PREDICTING THE REMAINING DISCHARGE TIME OF A BATTERY; U.S. Ser. No. 10/783,682, filed Feb. 20, 2004, entitled REPLACEABLE CLAMP FOR ELECTRONIC BATTERY TESTER; U.S. Ser. No. 10/791,141, filed Mar. 2, 2004, entitled METHOD AND APPARATUS FOR AUDITING A BATTERY TEST; U.S. Ser. No. 10/823,140, filed Apr. 13, 2004, entitled THEFT PREVENTION DEVICE FOR AUTOMOTIVE VEHICLE SERVICE CENTERS; U.S. Ser. No. 10/864,904, filed Jun. 9, 2004, entitled ALTERNATOR TESTER; U.S. Ser. No. 10/867,385, filed Jun. 14, 2004, entitled ENERGY MANAGEMENT SYSTEM FOR AUTOMOTIVE VEHICLE; U.S. Ser. No. 10/870,680, filed Jun. 17, 2004, entitled ELECTRONIC BATTERY TESTER WITH RELATIVE TEST OUTPUT; U.S. Ser. No. 10/883,019, filed Jul. 1, 2004, entitled MODULAR ELECTRONIC BATTERY TESTER; U.S. Ser. No. 10/896,835, filed Jul. 22, 2004, entitled BROAD-BAND LOW-INDUCTANCE CABLES FOR MAKING KELVIN CONNECTIONS TO ELECTROCHEMICAL CELLS AND BATTERIES; U.S. Ser. No. 10/896,834, filed Jul. 22, 2004, entitled ELECTRONIC BATTERY TESTER; U.S. Ser. No. 10/897,801, filed Jul. 23, 2004, entitled SHUNT CONNECTION TO A PCB FOR AN ENERGY MANAGEMENT SYSTEM EMPLOYED IN AN AUTOMOTIVE VEHICLE; U.S. Ser. No. 10/914,304, filed Aug. 9, 2004, entitled ELECTRONIC BATTERY TESTER WITH NETWORK COMMUNICATION; U.S. Ser. No. 10/958,821, filed Oct. 5, 2004, entitled IN-VEHICLE BATTERY MONITOR; U.S. Ser. No. 10/958,812, filed Oct. 5, 2004, entitled SCAN TOOL FOR ELECTRONIC BATTERY TESTER; U.S. Ser. No. 11/008,456, filed Dec. 9, 2004, entitled APPARATUS AND METHOD FOR PREDICTING BATTERY CAPACITY AND FITNESS FOR SERVICE FROM A BATTERY DYNAMIC PARAMETER AND A RECOVERY VOLTAGE DIFFERENTIAL, U.S. Ser. No. 60/587,232, filed Dec. 14, 2004, entitled CELLTRON ULTRA, U.S. Ser. No. 11/018,785, filed Dec. 21, 2004, entitled WIRELESS BATTERY MONITOR; U.S. Ser. No. 60/653,537, filed Feb. 16, 2005, entitled CUSTOMER MANAGED WARRANTY CODE; U.S. Ser. No. 11/063,247, filed Feb. 22, 2005, entitled ELECTRONIC BATTERY TESTER OR CHARGER WITH DATABUS CONNECTION; U.S. Ser. No. 60/665,070, filed Mar. 24, 2005, entitled OHMMETER PROTECTION CIRCUIT; U.S. Ser. No. 11/130,600, filed May 17, 2005, entitled QUERY BASED ELECTRONIC BATTERY TESTER; U.S. Ser. No. 11/141,234, filed May 31, 2005, entitled BATTERY TESTER CAPABLE OF IDENTIFYING FAULTY BATTERY POST ADAPTERS; U.S. Ser. No. 11/143,828, filed Jun. 2, 2005, entitled BATTERY TEST MODULE; U.S. Ser. No. 11/146,608, filed Jun. 7, 2005, entitled SCAN TOOL FOR ELECTRONIC BATTERY TESTER; U.S. Ser. No. 60/694,199, filed Jun. 27, 2005, entitled GEL BATTERY CONDUCTANCE COMPENSATION; U.S. Ser. No. 11/178,550, filed Jul. 11, 2005, entitled WIRELESS BATTERY TESTER/CHARGER; U.S. Ser. No. 60/705,389, filed Aug. 4, 2005, entitled PORTABLE TOOL THEFT PREVENTION SYSTEM, U.S. Ser. No. 11/207,419, filed Aug. 19, 2005, entitled SYSTEM FOR AUTOMATICALLY GATHERING BATTERY INFORMATION FOR USE DURING BATTERY TESTER/CHARGING, U.S. Ser. No. 60/712,322, filed Aug. 29, 2005, entitled AUTOMOTIVE VEHICLE ELECTRICAL SYSTEM DIAGNOSTIC DEVICE, U.S. Ser. No. 60/713,169, filed Aug. 31, 2005, entitled LOAD TESTER SIMULATION WITH DISCHARGE COMPENSATION, U.S. Ser. No. 60/731,881, filed Oct. 31, 2005, entitled PLUG-IN FEATURES FOR BATTERY TESTERS; U.S. Ser. No. 60/731,887, filed Oct. 31, 2005, entitled AUTOMOTIVE VEHICLE ELECTRICAL SYSTEM DIAGNOSTIC DEVICE; U.S. Ser. No. 11/304,004, filed Dec. 14, 2005, entitled BATTERY TESTER THAT CALCULATES ITS OWN REFERENCE VALUES; U.S. Ser. No. 60/751,853, filed Dec. 20, 2005, entitled BATTERY MONITORING SYSTEM; which are incorporated herein in their entirety.

The theft of portable devices, especially portable electronic devices, continues to be a widespread problem. Portable tools used by technicians in automotive vehicle service centers are generally mobile as well as expensive. The service center environment is often chaotic and includes a large quantity of people arriving and departing. Portable tools can easily be stolen without notice of those managing or working at the center.

SUMMARY OF THE INVENTION

An apparatus and method for preventing theft in automotive vehicle service centers includes a transmitter configured to transmit a wireless security signal which defines a perimeter. At least one portable tool having a receiver configured to receive the transmitted security signal. Security circuitry is actuated if the tool is outside and/or near the perimeter defined by the security signal.

Also provided is an apparatus and method for preventing theft in automotive vehicle service centers that include at least one portable tool and a controller. The portable tool includes circuitry configured to communicate with the controller. The portable tool further includes anti-theft circuitry, which is configured to disable the portable tool if no communication occurs between the portable tool and the controller for a predetermined time period.

In some of the present embodiments, in addition to at least one portable tool and the controller, a docking device is included. The portable tool is configured to communicate with the controller when it is installed in the docking device. Thus, after removal from the docking device, if the portable tool is not installed back in the docking device within a predetermined time period, the portable tool is disabled.

BRIEF DESCRIPTION OF THE DRAWINGS

FIG. 1-2 is a simplified block diagram of the theft prevention device of FIG. 1-1 after the theft has occurred in accordance with an embodiment of the present invention.

FIG. 2-1 is a simplified block diagram of a theft prevention device prior to a theft in accordance with an embodiment of the present invention.

FIG. 2-2 is a simplified block diagram of the theft prevention device of FIG. 2-1 after the theft has occurred in accordance with an embodiment of the present invention.

DETAILED DESCRIPTION OF THE PREFERRED EMBODIMENTS

Figure 1:
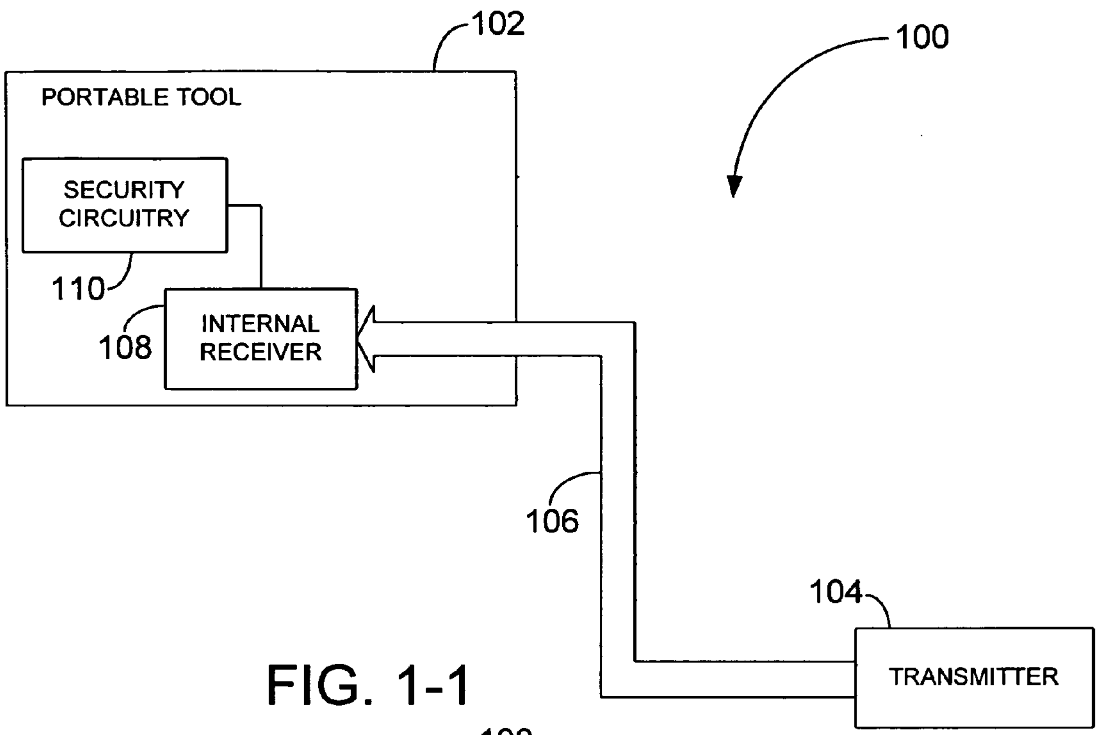
FIG. 1-1 is a simplified block diagram of a theft prevention device prior to a theft in accordance with an embodiment of the present invention.

FIG. 1-1 is a simplified block diagram of theft prevention device 100 prior to a theft in accordance with an embodiment of the present invention. Device 100 includes transmitter 104 configured to transmit a wireless security signal 106 that defines a perimeter. Device 100 also includes a receiver 108 embedded in portable tool 102 and operably coupled to security circuitry 110. Security signal 106 can be encoded with a key such that secure communication can take place between transmitter 104 and portable tool 102. The key can be randomly changeable to ensure secure communication. Security signal 106 can also transmit other information besides defining a perimeter. Examples of other information include software updates for the portable tool, messages for the operator and time updates.

Receiver 108 is configured to receive the transmitted security signal 106. If portable tool 102 remains located within the perimeter defined by the wireless security signal, then proper use and/or storage of portable tool 102 is being practiced within an automotive vehicle service center. If, however, portable tool 102 is carried outside the perimeter, a theft has occurred. For example, non-receipt of security signal 106 by receiver 108 can indicate that portable tool 102 is outside of the perimeter. In another example, receipt of security signal 106 having a signal strength less than a predetermined minimum signal strength can indicate that portable tool 102 is outside the perimeter. In FIG. 1-1, transmitter 104 is in communication with receiver 108 and the strength of security signal 106 is greater than the predetermined minimum signal strength. Therefore, portable tool 102 is located within the perimeter defined by security signal 106 and is in proper use.

Figures 1, 2:
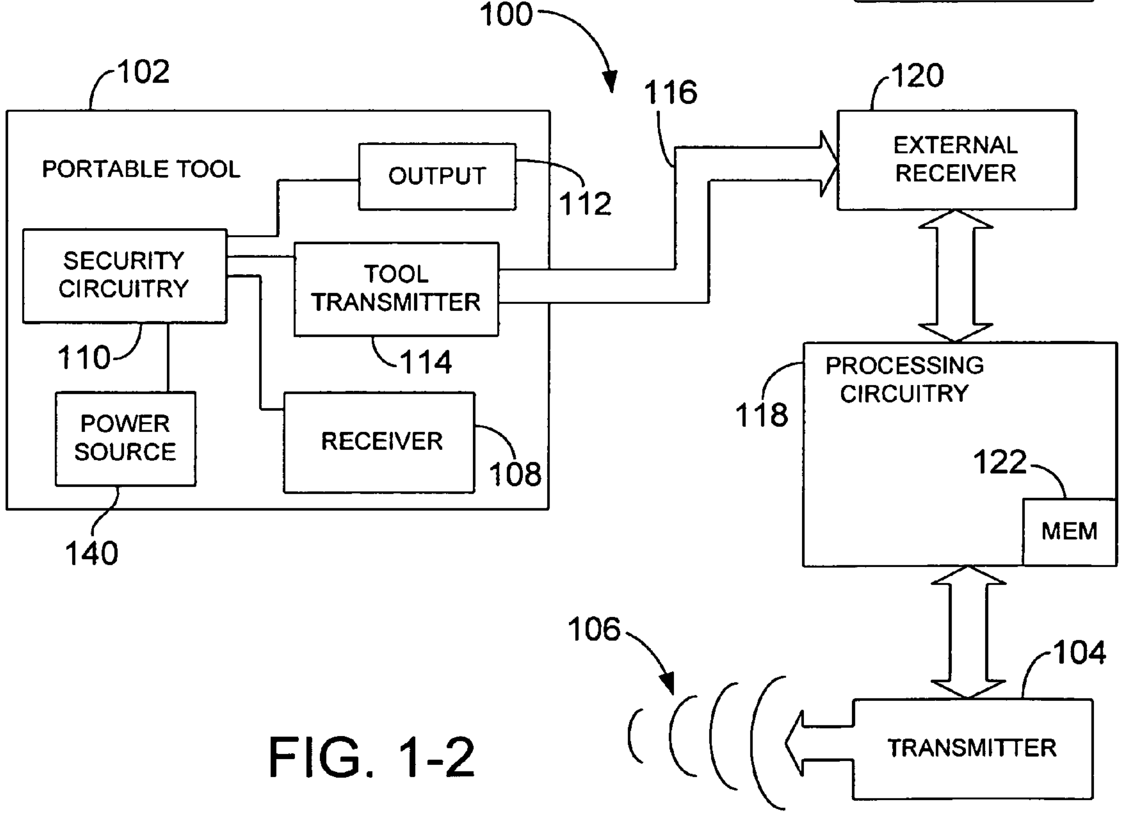
Figures 1, 2:
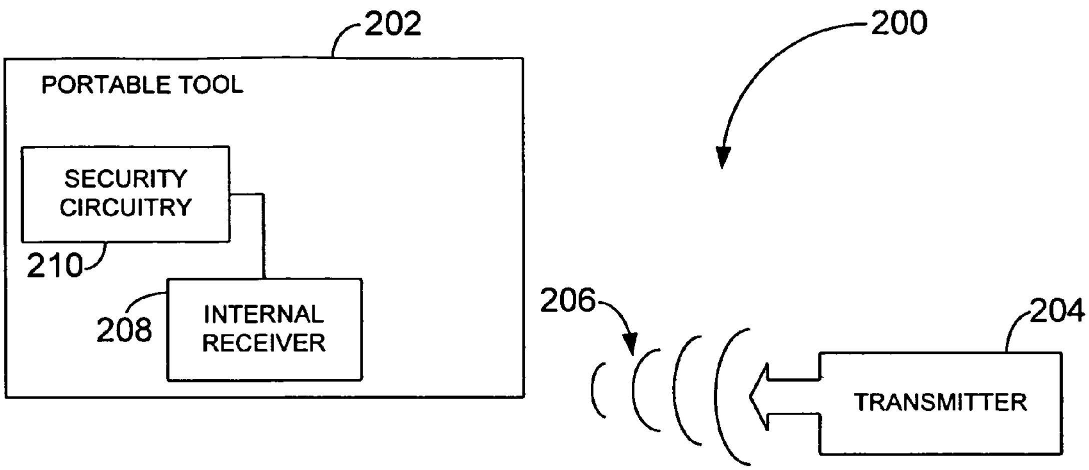
Figure 2:
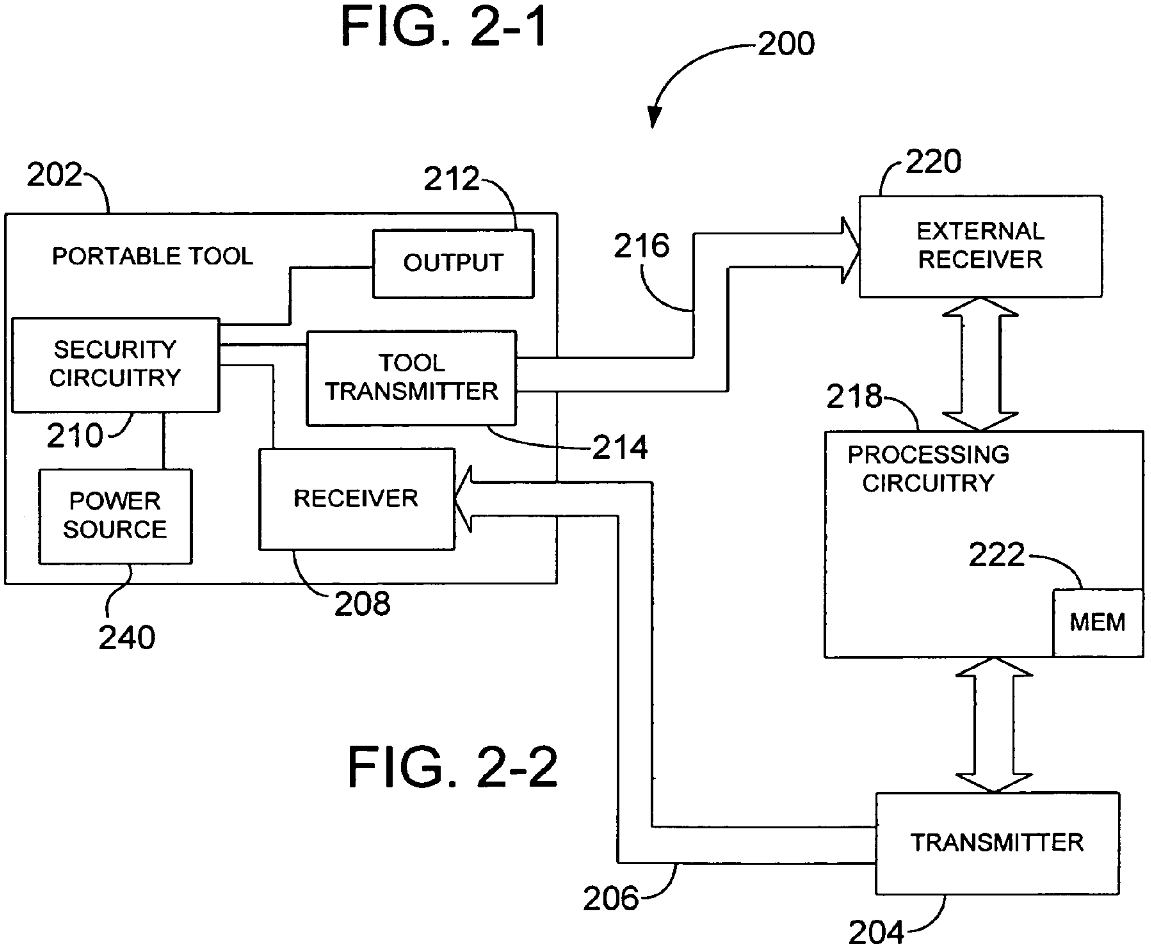

FIG. 1-2 is a simplified block diagram of theft prevention device 100 of FIG. 1-1 after the theft has occurred in accordance with an embodiment of the present invention. Portable tool 102 includes an output 112 operably coupled to security circuitry 110 and tool transmitter 114 operably coupled to security circuitry 110. Portable tool 102 also includes an internal power source 140 configured to supply power to security circuitry 110 such that portable tool can receive security signal 106, output the continuous audible noise and transmit theft signal 116. As illustrated in FIG. 1-2, transmitter 104 has either lost communication with receiver 108 or security signal 106 is less than the predetermined minimum signal strength. Therefore, a theft has occurred because portable tool 102 has been carried outside of the perimeter defined by security signal 106.

When a theft occurs, security circuitry 110 is configured to disable portable tool 102 causing the tool to become inoperable. For example, security circuitry 110 can disable portable tool 102 after the portable tool has been outside of the perimeter for a predetermined period of time. Waiting the predetermined period of time prevents portable tool 102 from disabling if there was a temporary interruption in security signal 106. In addition, security circuitry 110 instructs output 112 to emit a continuous audible noise. This continuous audible noise will alert service center employees that portable tool 102 has been stolen and alert others outside of the service center. Furthermore, when portable tool 102 is carried outside of the perimeter defined by security signal 106, security circuitry 110 instructs tool transmitter 114 to transmit theft signal 116. It should be noted that portable tool 102 can also be reset and/or overridden with a hardware or software key such that theft protection device 100 is disabled.

As illustrated in FIG. 1-2, device 100 further includes processing circuitry 118 operably coupled to transmitter 104 and external receiver 120 operably coupled to processing circuitry 118. External receiver 120 is configured to receive the transmitted theft signal 116. When external receiver 120 receives the transmitted theft signal 116, processing circuitry 118 is configured to output an audible alarm. In addition, processing circuitry 118 records in memory 122 information related to theft signal 116 for later user retrieval. For example, processing circuitry 118 can record a date and time when portable tool 102 was stolen. Processing circuitry 118 can also record a serial number or identification number related to the particular portable tool 102 stolen based on the received theft signal 116.

Both security signal 104 and theft signal 116 can include a variety of signals. For example, transmitter 104 and tool transmitter 114 can transmit a diffused infrared signal while receiver 108 and external receiver 120 can be configured to receive a diffused infrared signal. Diffused infrared signals utilize the walls and ceilings of a room to bounce infrared signals between a transmitter and a receiver. Thus, people walking about the room as well as fixed obstructions will not interfere with sustained infrared communications. However, transmitter 104, external receiver 120 and portable tool 102 must all be located in the same room because infrared communication can not penetrate obstructions, such as walls. In another example, transmitter 104 and tool transmitter 114 can transmit a radio frequency (RF) signal while receiver 108 and external receiver 120 can be configured to receive a RF signal. In this example, transmitter 104, external receiver 120 and portable tool 102 can all be located in different rooms because RF signals can easily penetrate walls and other obstructions. Two common standards for RF communication include the Bluetooth protocol and the 802.11(b) protocol. The Bluetooth protocol is cost-effective and easy to implement. However, the distance the Bluetooth signal covers is less than the distance covered by the 802.11(b) signal.

FIG. 2-1 is a simplified block diagram of theft prevention device 200 prior to a theft in accordance with an embodiment of the present invention. Device 200 includes transmitter 204 configured to transmit a wireless security signal 206 that defines a perimeter. Device 200 also includes a receiver 208 embedded in portable tool 202 and operably coupled to security circuitry 210. Security signal 206 can be encoded with a key such that secure communication can take place between transmitter 204 and portable tool 202. The key can be randomly changeable to ensure secure communication. Security signal 206 can also transmit other information besides defining a perimeter. Examples of other information include software updates for the portable tool, messages for the operator and time updates.

Receiver 208 is configured to receive the transmitted security signal 206. If portable tool 202 remains located outside the perimeter, then proper use and/or storage of portable tool 202 is being practiced within the automotive service center. If, however, portable tool 202 at least passes through the perimeter, a theft has occurred. For example, receipt of security signal 106 can indicate that portable tool 202 is within the perimeter defined by the security signal. In another example, receipt of security signal 106 having a signal strength greater than a predetermined minimum signal strength can indicate that portable tool 202 is located within the perimeter. In FIG. 2-1, transmitter 204 is not in communication with receiver 208 or security signal 206 has a signal strength less than the predetermined minimum signal strength. Therefore, portable tool 102 is located outside the perimeter defined by security signal 206 and is in proper use.

FIG. 2-2 is a simplified block diagram of theft prevention device 200 of FIG. 2-1 after a theft has occurred in accordance with an embodiment of the present invention. Portable tool 202 includes an output 212 operably coupled to security circuitry 210 as well as tool transmitter 214 operably coupled to security circuitry 210. Portable tool 202 also includes an internal power source 240 configured to supply power to security circuitry 210 such that portable tool can receive security signal 206, output the continuous audible noise and transmit theft signal 216. As illustrated in FIG. 2-2, transmitter 204 is in communication with receiver 208 or security signal 206 has a signal strength greater than the predetermined minimum signal strength. Therefore, portable tool 202 has at least partially passed through the perimeter defined by security signal 206 and a theft has occurred.

If a theft has occurred, security circuitry 210 is configured to disable portable tool 202 causing the tool to become inoperable. For example, security circuitry 110 can disable portable tool 102 after the portable tool has been outside of the perimeter for a predetermined period of time. Waiting the predetermined period of time prevents portable tool 102 from disabling if there was a temporary interruption in security signal 106. In addition, security circuitry 210 instructs output 212 to emit a continuous audible noise. This continuous audible noise will alert service center employees that portable tool 202 has been stolen and alert others outside of the service center. Furthermore, when portable tool 202 at least partially passes through the perimeter defined by security signal 206, security circuitry 210 instructs tool transmitter 214 to transmit theft signal 216. It should be noted that portable tool 202 can also be reset and/or overridden with a hardware or software key such that theft protection device 200 is disabled.

As illustrated in FIG. 2-2, device 200 further includes processing circuitry 218 operably coupled to transmitter 204 and external receiver 220 operably coupled to processing circuitry 218. External receiver 220 is configured to receive the transmitted theft signal 216. If external receiver 220 receives the transmitted theft signal 216, then processing circuitry 218 is configured to output an audible alarm. In addition, processing circuitry 218 records in memory 222 information related to theft signal 216 for later user retrieval. For example, processing circuitry 218 can record a date and time when portable tool 202 was stolen. In addition, theft signal 216 can include information related to identification of the particular portable tool 202 based on theft signal 216. Thus, processing circuitry 218 can also record a serial number or identification number related to the particular portable tool 202 stolen.

Both security signal 204 and theft signal 216 can include a variety of signals. For example, transmitter 204 and tool transmitter 214 can transmit a diffused infrared signal while receiver 208 and external receiver 220 can be configured to receive a diffused infrared signal. In another example, transmitter 204 can transmit a direct infrared signal (or beam of infrared light) and receiver 208 can be configured to receive the direct infrared signal. In another example, transmitter 204 and tool transmitter 214 can transmit a radio frequency (RF) signal while receiver 208 and external receiver 220 can be configured to receive a RF signal. Two common standards for RF communication include the Bluetooth protocol and the 802.11(b) protocol. In yet another example, receiver 208, tool transmitter 214 and security circuitry 210 can include a radio frequency identification (RFID) tag, while external receiver 220 and transmitter 204 can include a RFID reader. In this example, the RFID tag at least partially passes through the perimeter defined by security signal 206. The RFID tag detects security signal 206 and disables portable tool 202 from operation as well as instructs output 212 to emit a continuous audible noise as described above. After the RFID reader transmits RF signals to activate the tag, the RFID reader decodes the data encoded in the tag's security circuitry. The decoded data is passed to processing circuitry 218 for identification and reporting as well as causes processing circuitry to sound an audible alarm as discussed above.

Figure 3:
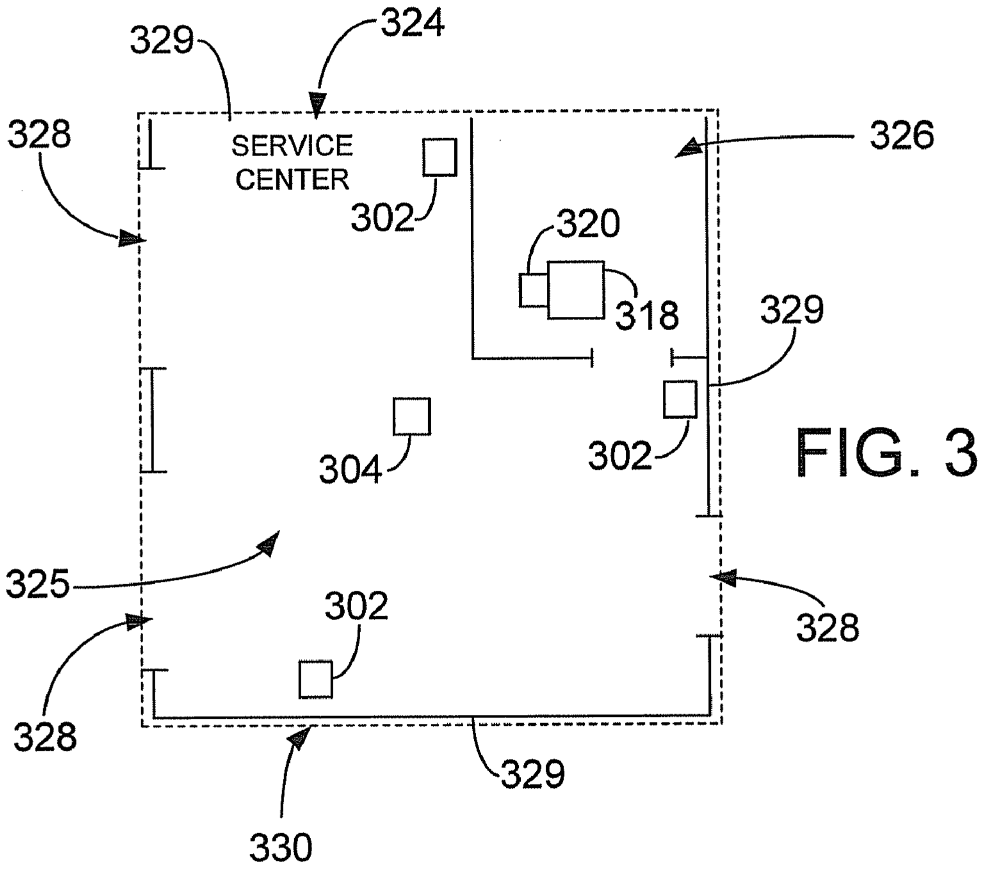
FIG. 3 is a simplified block diagram of an automotive vehicle service center in accordance with an embodiment of the present invention.

FIG. 3 is a simplified block diagram of automotive service center 324. Automotive service center 324 includes repair area 325 as well as inner office space 326. Service center 324 also includes a plurality of exits and entrances 328 around outer walls 329 of center 324. As illustrated in FIG. 3, transmitter 304 is located in repair area 325 and is transmitting a security signal (FIGS. 1-1 and 1-2). The security signal defines a perimeter represented by dashed line 330. A plurality of portable tools 302 are located about repair area 325. Each portable tool 302 receives the security signal with an receiver (FIGS. 1-1 and 1-2). If a person were to pick up at least one of the plurality of tools 302 and carry tool 302 outside of dashed line 330, then the security circuitry (FIGS. 1-1 and 1-2) of that particular portable tool 302 would disable the tool. Therefore, portable tool 302 is rendered inoperable. In addition, the security circuitry instructs an output (FIGS. 1-1 and 1-2) to emit a continuous audible noise.

Furthermore, when a person carries at least one portable tool 302 outside of the dashed line, the security circuitry instructs a tool transmitter (FIGS. 1-1 and 1-2) embedded within portable tool 302 to transmit a theft signal (FIGS. 1-1 and 1-2). An external receiver 320 located within inner office space 326 and operably coupled to processing circuitry 318 is configured to receive the transmitted theft signal. Upon receipt of the theft signal by external receiver 320, processing circuitry 318 records information related to the theft signal as well as outputs an audible alarm. In accordance with FIG. 3, the security signal can be a diffused infrared signal or a RF signal. The theft signal can be a RF signal but not an infrared signal since infrared signal can not penetrate the walls of inner office space 326. Those skilled in the art will recognize that the theft signal could be a diffused infrared signal if the external receiver were located in repair area 325. Communication between external receiver 320 and processing circuitry 318 and between the transmitter 304 and processing circuitry can be any type of cable connection as well as any type of wireless connection.

Figure 4:
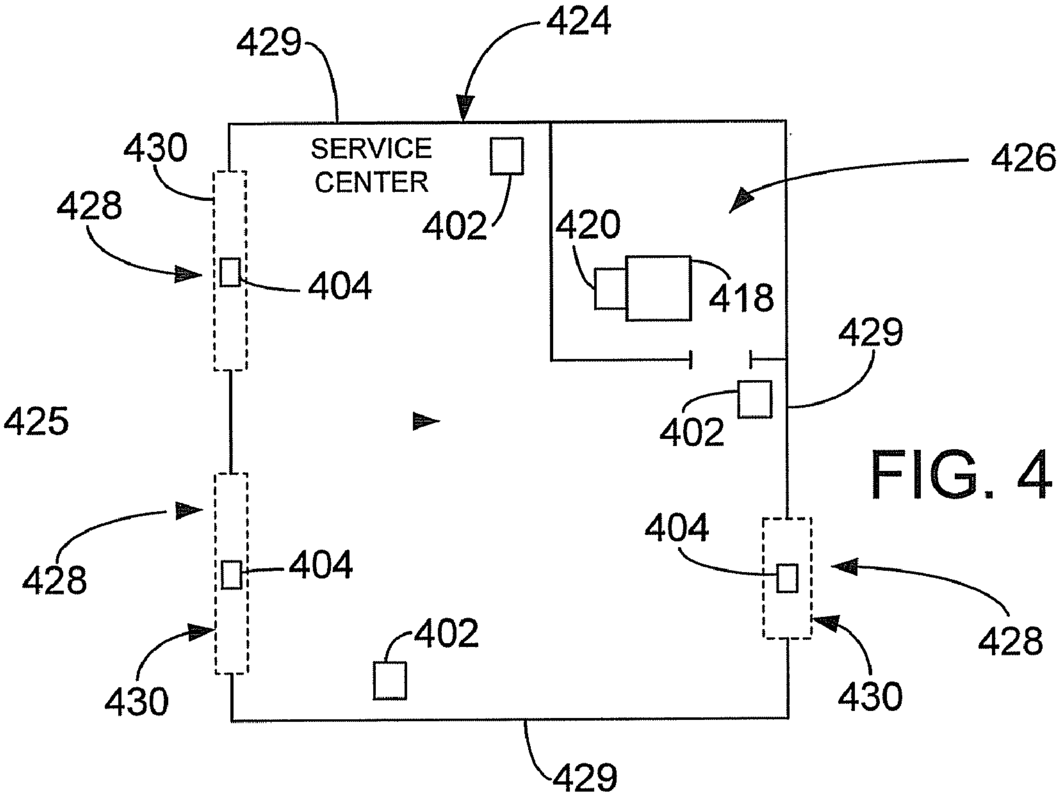
FIG. 4 is a simplified block diagram of an automotive vehicle service center in accordance with an embodiment of the present invention.

FIG. 4 is a simplified block diagram of automotive service center 424. Automotive service center 424 includes repair area 425 as well as inner office space 426. Service center 424 also includes a plurality of exits and entrances 428 around the outer walls 429 of center 424. FIG. 4 also illustrates a plurality of transmitters 404. Each transmitter 404 is located within each exit and entrance 428. Each transmitter 404 is configured to transmit a security signal (FIGS. 2-1 and 2-2). Each security signal defines a perimeter represented by dashed lines 430. A plurality of portable tools 402 are located about repair area 425. Each portable tool 402 is configured to receive the security signal with a receiver (FIGS. 2-1 and 2-2). If a person were to pick up at least one of the plurality of tools 402 and carry it through an entrance or exit 428, then tool 402 would at least pass partially through one of the perimeters illustrated by dashed line 430. Upon passing at least partially through one perimeter, the security circuitry (FIGS. 2-1 and 2-2) of that particular portable tool 402 would disable the tool. Therefore, portable tool 402 is rendered inoperable. In addition, the security circuitry instructs an output (FIGS. 2-1 and 2-2) to emit a continuous audible noise.

Furthermore, if a person carries at least one portable tool 402 at least partially through an entrance or exit 428, the security circuitry instructs a tool transmitter (FIGS. 2-1 and 2-2) embedded within portable tool 402 to transmit a theft signal (FIGS. 2-1 and 2-2). An external receiver 420 located within inner office space 426 and operably coupled to processing circuitry 418 is configured to receive the transmitted theft signal. Upon receipt of the theft signal by external receiver 420, processing circuitry 418 records information related to the theft signal as well as outputs an audible alarm. In accordance with FIG. 4, the security signal can be a diffused infrared signals or a RF signal. The theft signal can be a RF signal but not an infrared signal since an infrared signal can not penetrate the walls of inner office space 426. Those skilled in the art will recognize that the theft signal could be a diffused infrared signal if the external receiver were located in repair area 405. Communication between external receiver 420 and processing circuitry 418 and between the transmitter 404 and the processing circuitry can be any type of cable connection as well as a type of wireless connection.

Figure 5:
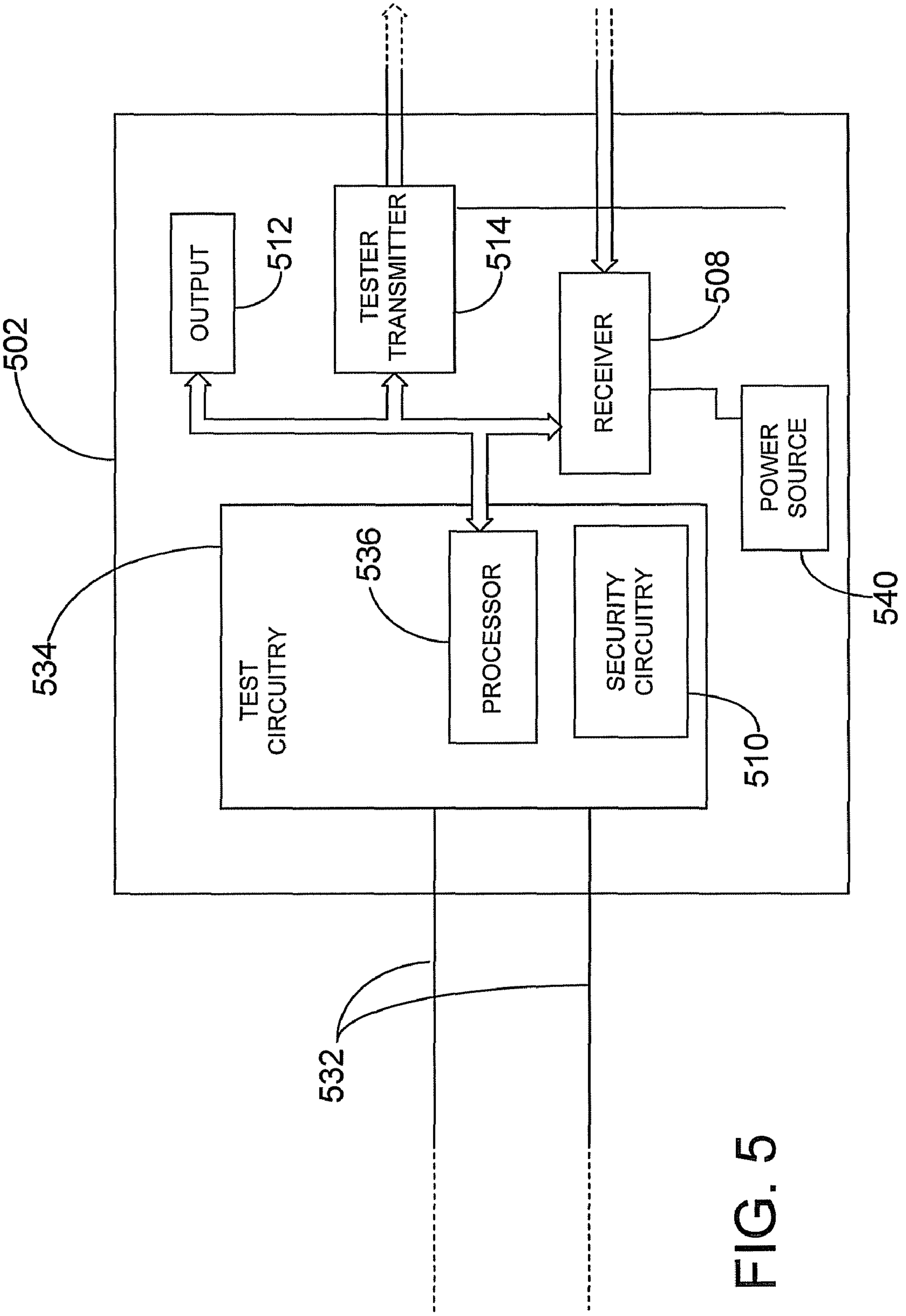
FIG. 5 is a simplified block diagram of an electronic battery tester in accordance with embodiment of the present invention.

FIG. 5 is a simplified block diagram of an example electronic battery tester 502 with which embodiments of the present invention are useful. Battery tester 502 is a type of portable tool which couples to a battery (not shown) via connectors 532. For example, connectors 532 may provide Kelvin connections to a battery. Note that FIG. 5 is illustrative of a specific type of battery tester which measures dynamic parameters. However, in one aspect, the present invention is applicable to any type of battery tester including those which do not use dynamic parameters. Other types of example testers include testers that conduct load tests, current based tests, voltage based tests, tests which apply various conditions or observe various performance parameters of a battery, etc.

Battery tester 502 includes test circuitry 534. Test circuitry 534 contains processor 536, security circuitry 510 and other circuitry configured to measure a dynamic parameter of a battery. As used herein, a dynamic parameter is one which is related to a signal having a time varying component. The signal can be either applied to or drawn from the battery.

Besides assisting in measuring dynamic and non-dynamic parameters of the battery, processor 536 also controls the operation of other components, such as theft prevention components, within battery tester 502. Battery tester 502 also includes output 512, tester transmitter 514 and receiver 508. Processor 536 controls the operation of these theft prevention components as well as carries out different battery testing functions. Battery tester 502 also includes internal power source 540. Generally, processor 536 draws its power from the battery being tested when in operation. However, battery tester 502 includes power source 540 such that processor 536 can control security circuitry 510, output 512, tester transmitter 514 and receiver 508 when battery tester 502 is not coupled to a battery being tested.

In some embodiments of the present invention, tool transmitter 514 is configured to transmit an infrared or RF signal and receiver 508 is configured to receive an infrared or RF signal. In this example, the theft prevention components rely on an internal power source 540 in order to complete the theft prevention operations as described in FIGS. 1-4. In other embodiments of the present invention, tool transmitter 514, receiver 508 and security circuitry 510 include a RFID tag. In this example, the theft prevention components rely on a reader to supply power in order to complete the theft prevention operations. Thus, no internal power source is needed.

Figure 6:
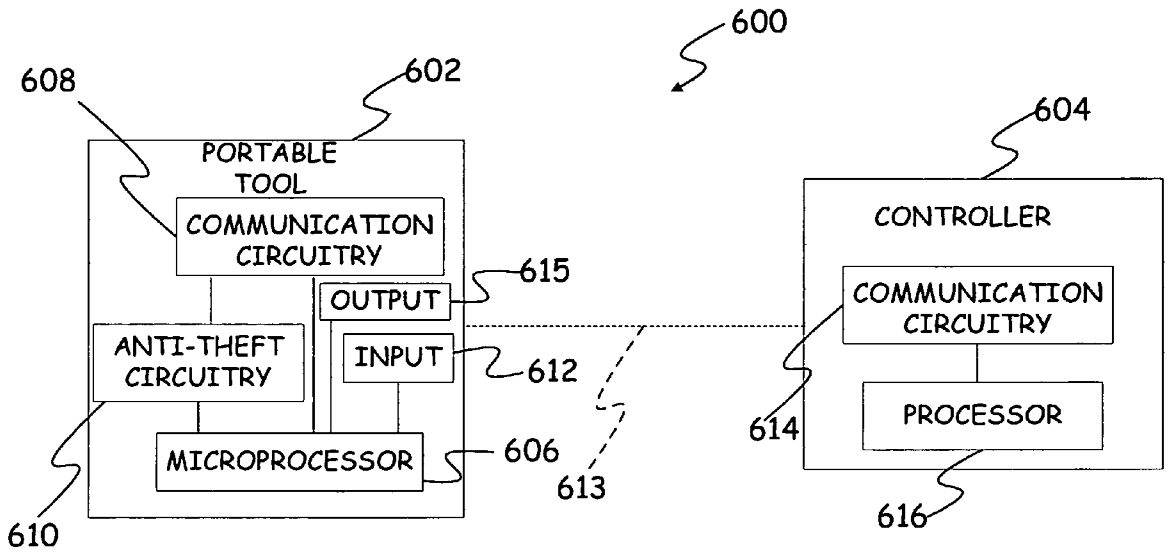
FIG. 6 is a simplified block diagram of a theft prevention system in accordance with the present invention.

FIG. 6 is a simplified block diagram of a theft prevention system 600 in accordance with another embodiment of the present invention. As can be seen in FIG. 6, system 600 includes at least one portable tool such as tool 602 and a controller 604, which can include a personal computer and communication circuitry. Example portable tool 602 includes a microprocessor 606, communication circuitry 608, anti-theft circuitry 610, input 612 and output 615. Example portable tool 602, in some embodiments, includes an internal power source (not shown in FIG. 6). Portable tool 602, with the help of tool communication circuitry 608, is configured to communicate with controller 604, which includes controller communication circuitry 614 and processor 616. Communication between portable tool 602 and controller 604 takes place via communication link 613, which can be any suitable wired or wireless communication link that is currently known or will be developed in the future. In some of the present embodiments, anti-theft circuitry 610 is configured to disable one or more functions of portable tool 602 if no communication occurs between portable tool 602 and controller 604 for a predetermined time period. The predetermined time period can be programmed into tool 602 with the help of a suitable input (keypad, for example) 612. In some embodiments, anti-theft circuitry 610 can instruct output 615 to emit a continuous audible noise if there is no communication between portable tool 602 and controller 604 for a predetermined time period. In some of the present embodiments, in addition to at least one portable tool 602 and the controller 604, a docking device for portable tools such as 602 is included.

Figure 7:
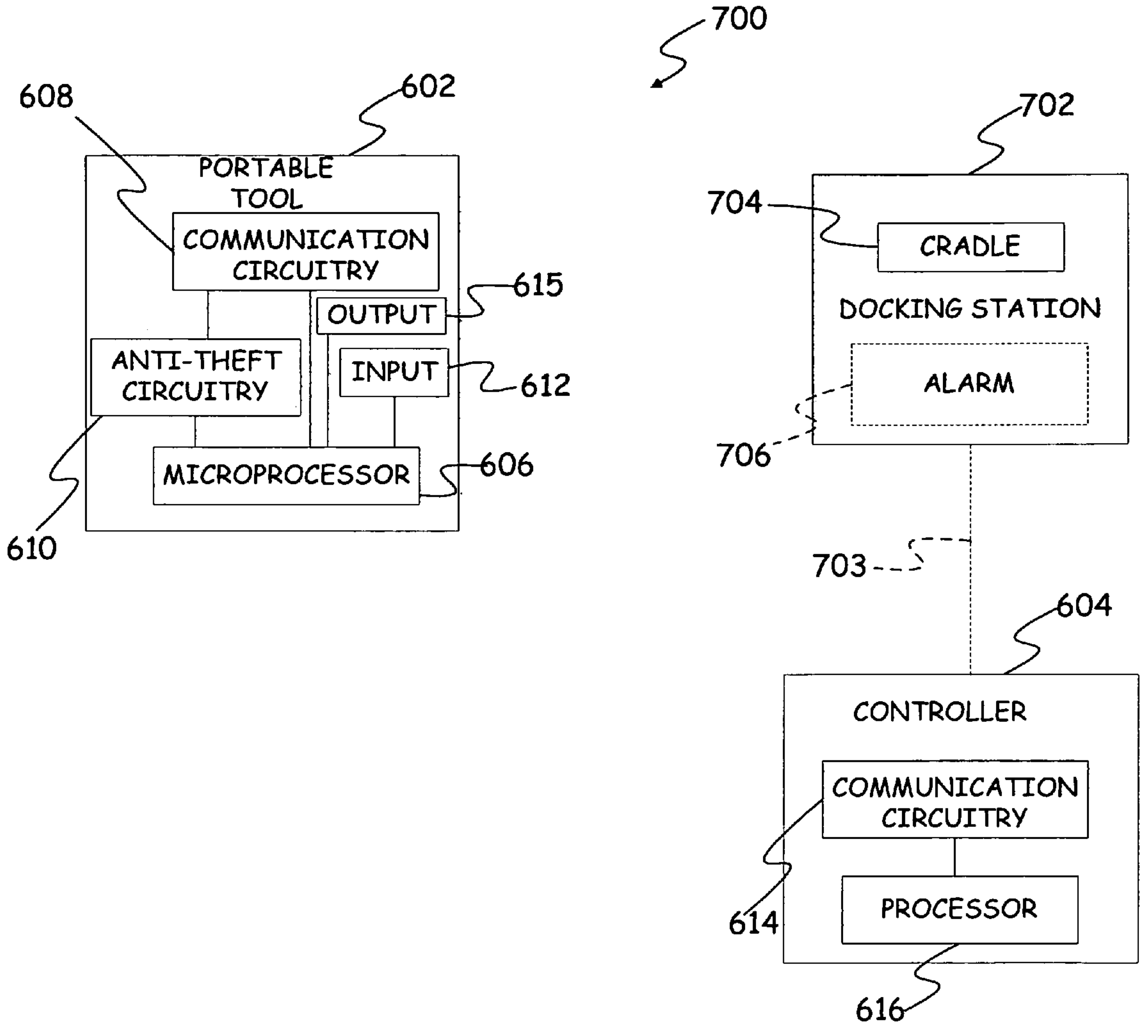
FIG. 7 is a simplified block diagram of the theft prevention device of FIG. 6 with an additional docking station in accordance with an embodiment of the present invention.

FIG. 7 is a simplified block diagram of a theft prevention system 700 with an additional docking device 702 in accordance with one of the present embodiments. In the embodiment shown in FIG. 7, portable tool 602 is configured to communicate with controller 604 when it is installed in docking device or docking station 702. Specifically, in some of the present embodiments, portable tool 602 can be installed in a cradle 704 of docking device 702 and begins communicating with controller 604 upon installation in cradle 704. In some embodiments, communication between portable tool 602 and controller 604 terminates upon removal of portable tool 602 from cradle 704. After removal from docking device 702, if portable tool 602 is not installed back in docking device 702 within a predetermined time period, portable tool 602 is disabled by anti-theft circuitry 610. It should be noted that disabling portable tool 602 can include disabling one or more functions that can be carried out by portable tool 602 or preventing a user for powering up portable tool 602. Docking device 702 can facilitate wireless or wired communication, via communication link 703, between portable tool 602 and controller 604. In embodiments of the present invention, docking station 602 can include an alarm (sound device, for example) 706 that is configured to create an audible alarm when portable tool 602 is removed from cradle 704 and/or when portable tool 602 has not been returned to cradle 704 within a pre-programmed timeframe.

In the above-described embodiments, once disabled, portable tool 602 can be reset by entering a reactivation code, which may be generated by controller 604. The reactivation code can be entered via input 612, which is configured to receive the reactivation code and to provide it to processor 606 of portable tool 602, which is configured to re-enable portable tool 602 upon receipt of the reactivation code.

In embodiments of the present invention, instead of disabling portable tool 602 after a predetermined time period, portable tool 602 may be disabled after it carries out one or more predetermined functions. For example, if portable tool 602 is a battery tester, it can be disabled after it carries out a battery test and sends the test results to controller 604. In such embodiments, a reactivation code will have to be entered via input 612 before carrying out each battery test.

Details regarding different types of portable tools and controllers (devices external to the portable tool that include communication circuitry (having a transmitter and/or receiver), processing circuitry, a memory, etc.) provided earlier in connection with FIGS. 1 through 5 are also applicable to the embodiments shown in FIGS. 6 and 7. Further, earlier-provided examples of a number of Infrared (IR) and Radio Frequency (RF) wireless communication techniques are also applicable to the embodiments of FIGS. 6 and 7. Also, in some of the present embodiments, controller 604 may be a server, which may, in turn, be coupled to other servers and/or I/O devices such as printers, etc. Details regarding a portable battery charger, which is another example portable tool embodiment, and included below in connection with FIG. 8.

Figure 8:
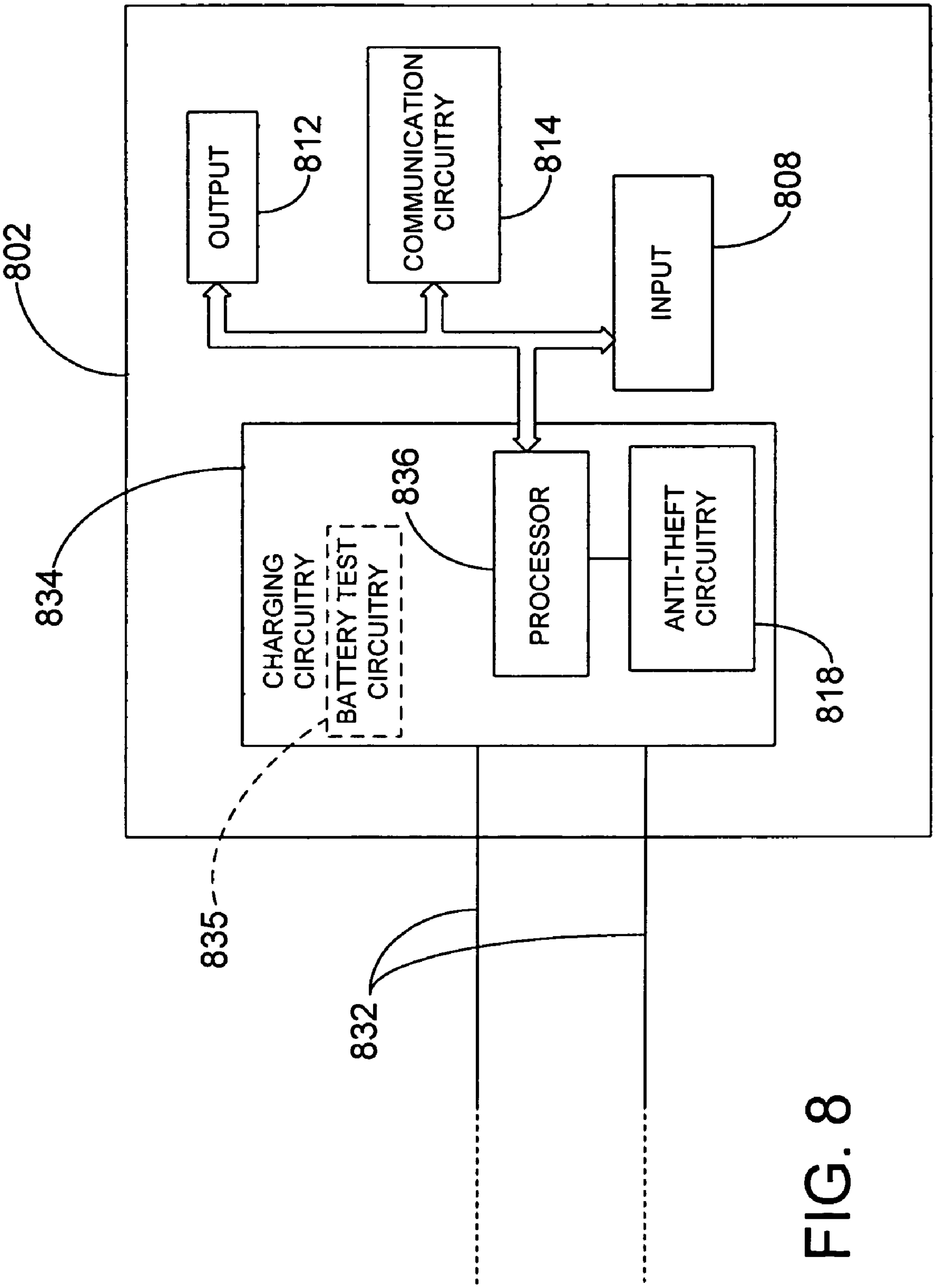
FIG. 8 is a simplified block diagram of an electronic battery charger in accordance with one of the present embodiments.

FIG. 8 is a simplified block diagram of an example electronic battery charger 802 with which the present embodiments are useful. Battery charger 802 is a type of portable tool which couples to a battery (not shown) via connectors 832, which may be Kelvin connectors.

Battery charger 802 includes charging circuitry 834. Charging circuitry 834 contains processor 836, anti-theft or security circuitry 818 and, in some embodiments, battery test circuitry 835, which is used to test the battery before and/or after charging it.

Processor 836 controls charging circuitry 834 and also controls the operation of other components, such as theft prevention components, within battery charger 802. Battery charger 802 also includes input 808, output 812 and communication circuitry 814. One example battery charger, that employs battery charging components which can be utilized as a part of circuitry 834, is set forth in U.S. Pat. No. 6,104,167, issued Aug. 15, 2000, and entitled "METHOD AND APPARATUS FOR CHARGING A BATTERY" which is incorporated herein by reference.

Figure 9:
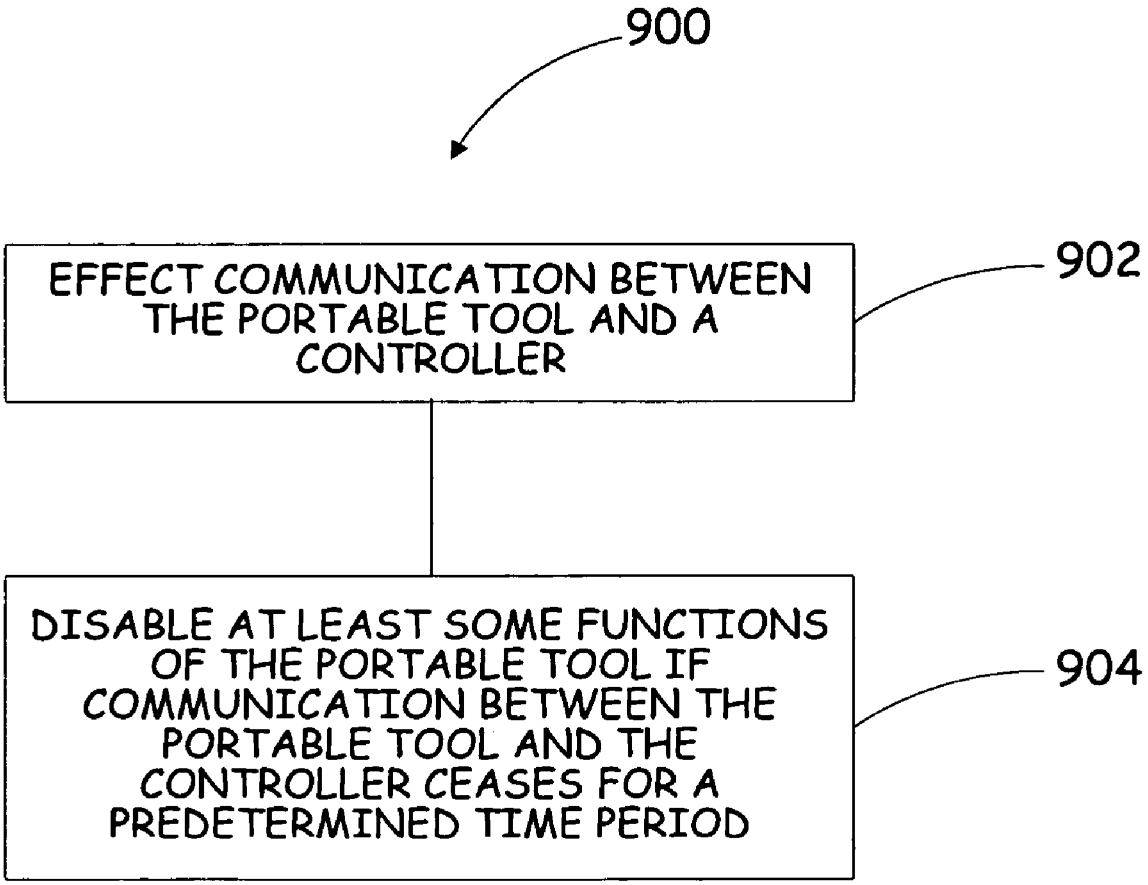
FIG. 9 is a flowchart of a method embodiment of the present invention.

FIG. 9 is a flowchart 900 of a method of preventing theft of a portable tool from an automotive vehicle service center. At step 902, communication between the portable tool and a controller is effected. At step 904, the portable tool is disabled if communication between the portable tool and the controller ceases for a predetermined time period. In some embodiments, effecting communication between the portable tool and the controller includes initiating communication between the portable tool and the controller when the portable tool is installed in a cradle of a docking station. In some embodiments, termination of communication between the portable tool and the controller occurs when the portable tool is removed from the cradle of the docking station. Different techniques, some of which are set forth above, can be employed to carry out the steps shown in the above flowchart while maintaining substantially the same functionality without departing from the scope and spirit of the present invention.

Although the present invention has been described with reference to preferred embodiments, workers skilled in the art will recognize that changes may be made in form and detail without departing from the spirit and scope of the invention.

What is claimed is:

1. An apparatus for preventing theft in automotive vehicle retail and service centers comprising:

a controller;

at least one portable tool for use in the automotive vehicle service centers;

a docking device for the at least one portable tool, the docking device having a cradle and an alarm therein; and a communication link between the docking device and the controller, wherein the at least one portable tool and the docking device, having the cradle and the alarm, are configured to initiate communication between the at least one portable tool and the controller, via the communication link between the docking device and the controller, when the at least one portable tool is installed in the cradle of the docking device, and physical contact occurs between electrical contacts in the at lest one portable tool and electrical contacts in the cradle of the docking station, wherein the at least one portable tool and the docking device are further configured to terminate communication between the at least one portable tool and the controller when the at least one portable tool is removed from the cradle of the docking device, and physical contact between electrical contacts in the at least one portable tool and the electrical contacts in the cradle of the docking station is eliminated, and wherein the at least one portable tool comprises anti-theft circuitry configured to disable at least one function of the at least one portable tool if no communication occurs between the at least one portable tool and the controller for a predetermined time period as a result of removal of the at least one portable tool from the cradle of the docking device, and wherein the predetermined time period is pre-programmable into the portable tool.

2. The apparatus of claim 1 wherein the docking device facilitates wired communication between the at least one portable tool and the controller.

3. The apparatus of claim 1 wherein the docking device facilitates wireless communication between the at least one portable tool and the controller.

4. The apparatus of claim 1 wherein the alarm is further configured to output a continuous audible noise if the tool is removed from the docking device for the predetermined time period.

5. A method of preventing theft of a portable tool from an automotive vehicle service center, the method comprising:

initiating communication between the portable tool and a controller when the portable tool is installed in a cradle of a docking station and, as a result of the installation of the portable tool in the cradle of the docking station, physical contact occurs between electrical contacts in the portable tool and electrical contacts in the cradle of the docking station;

terminating communication between the portable tool and the controller when the portable tool is removed from the cradle of the docking station and the removal of the portable tool from the cradle from the cradle of the docking station results in elimination of physical contact between the electrical contacts in the portable tool and the electrical contacts in the cradle of the docking station;

disabling, by circuitry within the portable tool, at least some functions of the portable tool if communication between the portable tool and the controller ceases for a predetermined time period as a result of removal of the at least one portable tool from the cradle of the docking station; and pre-programming the predetermined time period into the portable tool.

6. The method of claim 5 and further comprising generating a reactivation code.

7. The method of claim 6 and further comprising re-enabling the portable tool by entering the reactivation code into an input of the portable tool.

8. The method of claim 5 wherein the portable tool is one of a battery tester and a battery charger.

* * * * *